United States Patent
Russell et al.

(10) Patent No.: US 11,499,016 B2
(45) Date of Patent: Nov. 15, 2022

(54) POLYSULFONE-URETHANE COPOLYMER, MEMBRANES AND PRODUCTS INCORPORATING SAME, AND METHODS FOR MAKING AND USING SAME

(71) Applicant: Fresenius Medical Care Holdings, Inc., Waltham, MA (US)

(72) Inventors: Geoffrey Russell, Ogden, UT (US); James White, Ogden, UT (US); Jiunn Teo, Pleasant View, UT (US); Kevin Hudson, North Ogden, UT (US); Monica Hall, Ogden, UT (US); Praveen Kosaraju, Farmington, UT (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 308 days.

(21) Appl. No.: 17/060,212

(22) Filed: Oct. 1, 2020

(65) Prior Publication Data
US 2021/0017340 A1  Jan. 21, 2021

Related U.S. Application Data

(63) Continuation of application No. 16/145,225, filed on Sep. 28, 2018, now Pat. No. 10,822,461.
(Continued)

(51) Int. Cl.
*C08G 81/00* (2006.01)
*C08G 18/50* (2006.01)
(Continued)

(52) U.S. Cl.
CPC .......... *C08G 81/00* (2013.01); *B01D 67/0011* (2013.01); *B01D 67/0013* (2013.01);
(Continued)

(58) Field of Classification Search
CPC .................. C08G 18/87; C08G 18/3872; C08G 18/6666; C08L 75/04–10; C08L 81/06; C08J 2375/04–10; C08J 2381/06
See application file for complete search history.

(56) References Cited

U.S. PATENT DOCUMENTS 3,011,997 A   12/1961   De Witt
3,579,591 A   5/1971   Schnell et al.
(Continued)

FOREIGN PATENT DOCUMENTS

CN   1505646 A    6/2004
CN   103328526 A  9/2013
(Continued)

OTHER PUBLICATIONS

Office Action issued in corresponding Japanese Patent Application No. 2020-519360 dated Mar. 16, 2021 (with partial English translation)(7 pages).
(Continued)

*Primary Examiner* — Michael M Dollinger
(74) *Attorney, Agent, or Firm* — Kilyk & Bowersox, P.L.L.C.

(57) ABSTRACT

A polysulfone-urethane copolymer is disclosed, which can be used as a membrane polymer, e.g., a matrix polymer, a pore forming agent, or both, while enhancing a membrane's blood compatibility. Methods are disclosed for forming the copolymer and incorporating the copolymer in membranes (e.g., spun hollow fibers, flat membranes) and other products.

21 Claims, 7 Drawing Sheets

Scheme 1

(1a) D + G ⟶ D-G-D
(2a) D-G-D + D + $_{xs}$E ⟶ E-(D-E)$_{x1}$-(D-G-D)$_{y1}$-(E-D)$_{x2}$-E x1=1-100, e.g., 10-100, y1=1-100, e.g., 1-10, x2=1-100, e.g., 10-100

Scheme 2

(1b) $_{xs}$D + E ⟶ D-(D-E)$_{x3}$-D + D
(2b) G + D + D-(D-E)$_{x3}$-D ⟶ [D-(E-D)$_{x4}$-(G)$_{m3}$-(D-E)$_{x5}$]$_{x9}$-D x3=1-100, e.g., 10-30, x4=1-100, e.g., 10-30, m3=1-100, e.g., 1-10,
x5=1-100, e.g., 10-30, x9=1-100, e.g., 1-10

Scheme 3

(1c) D + $_{xs}$E ⟶ E-(D-E)$_{x6}$-D-E
(2c) D + G ⟶ D-G-D
(3c) E-(D-E)$_{x6}$-D-E + D-G-D ⟶ E-(D-E)$_{x7}$-D-E-(D-G-D)$_{m4}$-(E-D)$_{x8}$-D-E x6=1-100, e.g., 10-30, x7=1-100, e.g., 10-30,
m4=1-100, e.g., 1-10, x8=1-100, e.g., 10-30

Related U.S. Application Data

(60) Provisional application No. 62/568,556, filed on Oct. 5, 2017.

(51) Int. Cl.

| | | |
|---|---|---|
| *B01D 71/54* | (2006.01) | |
| *C08G 18/76* | (2006.01) | |
| *B01D 71/76* | (2006.01) | |
| *B01D 71/52* | (2006.01) | |
| *B01D 67/00* | (2006.01) | |
| *B01D 69/06* | (2006.01) | |
| *B01D 71/68* | (2006.01) | |
| *C08J 5/18* | (2006.01) | |
| *C08L 75/04* | (2006.01) | |
| *C08L 81/06* | (2006.01) | |
| *B01D 61/24* | (2006.01) | |
| *A61M 1/16* | (2006.01) | |
| *A61M 1/34* | (2006.01) | |

(52) U.S. Cl.
CPC .......... *B01D 69/06* (2013.01); *B01D 71/52* (2013.01); *B01D 71/54* (2013.01); *B01D 71/68* (2013.01); *B01D 71/76* (2013.01); *C08G 18/5072* (2013.01); *C08G 18/7657* (2013.01); *C08J 5/18* (2013.01); *C08L 75/04* (2013.01); *C08L 81/06* (2013.01); *A61M 1/1698* (2013.01); *A61M 1/34* (2013.01); *B01D 61/24* (2013.01); *C08J 2375/04* (2013.01); *C08J 2381/08* (2013.01); *C08J 2439/06* (2013.01)

(56) References Cited

U.S. PATENT DOCUMENTS

| | | | |
|---|---|---|---|
| 3,615,024 A | 10/1971 | Michaels | |
| 3,691,068 A | 9/1972 | Cross | |
| 3,770,850 A | 11/1973 | White | |
| 4,051,300 A | 9/1977 | Klein et al. | |
| 4,075,119 A | 2/1978 | Schmidt et al. | |
| 4,303,776 A | 12/1981 | Baron et al. | |
| 4,680,369 A * | 7/1987 | Kajimoto | C08G 18/3863 528/85 |
| 4,780,522 A * | 10/1988 | Kajimoto | G02B 1/043 528/85 |
| 4,906,375 A | 3/1990 | Heilmann | |
| 5,480,598 A | 1/1996 | Gentile et al. | |
| 5,547,576 A | 8/1996 | Onishi et al. | |
| 5,698,161 A | 12/1997 | Montoya | |
| 5,801,063 A | 9/1998 | Grandies et al. | |
| 5,919,370 A | 7/1999 | Röttger et al. | |
| 5,980,478 A | 11/1999 | Gorsuch et al. | |
| 6,040,415 A | 3/2000 | Arimori et al. | |
| 6,099,734 A | 8/2000 | Boggs et al. | |
| 6,214,290 B1 | 4/2001 | Esposito | |
| 6,267,926 B1 | 7/2001 | Reed et al. | |
| 6,478,960 B1 | 11/2002 | Saruhashi et al. | |
| 6,562,616 B1 | 5/2003 | Toner et al. | |
| 6,682,656 B2 | 1/2004 | Rothman et al. | |
| 6,802,971 B2 | 10/2004 | Gorsuch et al. | |
| 6,866,783 B2 | 3/2005 | Baurmeister et al. | |
| 6,869,412 B2 | 3/2005 | Ross | |
| 6,899,834 B2 | 5/2005 | Boggs et al. | |
| 6,918,886 B1 | 7/2005 | Baurmeister | |
| 6,992,138 B2 | 1/2006 | Tsuji et al. | |
| 7,108,787 B2 | 9/2006 | Nakabayashi et al. | |
| 7,273,465 B2 | 9/2007 | Ash | |
| 8,070,769 B2 | 12/2011 | Broome | |
| 8,071,683 B2 | 12/2011 | Mullick et al. | |
| 8,202,248 B2 | 6/2012 | Burnett et al. | |
| 8,425,838 B2 | 4/2013 | Mizoguchi et al. | |
| 8,444,586 B2 | 5/2013 | Beck | |
| 8,527,026 B2 | 9/2013 | Shults et al. | |
| 8,528,744 B2 | 9/2013 | Krause et al. | |
| 8,613,361 B2 | 12/2013 | Ueno et al. | |
| 8,877,062 B2 | 11/2014 | Mullick et al. | |
| 8,999,167 B2 | 4/2015 | Nakano et al. | |
| 9,066,697 B2 | 6/2015 | Peyser et al. | |
| 2002/0090389 A1 | 7/2002 | Humes et al. | |
| 2004/0007540 A1 | 1/2004 | Verpoort et al. | |
| 2004/0185257 A1 | 9/2004 | DeGrado et al. | |
| 2004/0213985 A1 | 10/2004 | Lee et al. | |
| 2005/0129731 A1 | 6/2005 | Horres et al. | |
| 2005/0187508 A1 | 8/2005 | Gorsuch et al. | |
| 2005/0274665 A1 | 12/2005 | Heilmann et al. | |
| 2006/0234582 A1 | 10/2006 | Gohl et al. | |
| 2006/0240239 A1 | 10/2006 | McGrail et al. | |
| 2006/0264355 A1 | 11/2006 | Storr et al. | |
| 2008/0135481 A1 | 6/2008 | Steiger et al. | |
| 2008/0142429 A1 | 6/2008 | Zhang et al. | |
| 2008/0142442 A1 | 6/2008 | Steiger et al. | |
| 2008/0142443 A1 | 6/2008 | Steiger et al. | |
| 2009/0081296 A1 | 3/2009 | Humes et al. | |
| 2009/0277850 A1 | 11/2009 | Adams et al. | |
| 2010/0016778 A1 | 1/2010 | Chattopadhyay | |
| 2010/0044314 A1 | 2/2010 | Zhang et al. | |
| 2010/0111761 A1 | 5/2010 | Correia De Pinho | |
| 2010/0280341 A1 | 11/2010 | Boock | |
| 2010/0316988 A1 | 12/2010 | Sehgal | |
| 2010/0326915 A2 | 12/2010 | Fislage et al. | |
| 2011/0015610 A1 | 1/2011 | Plahey et al. | |
| 2011/0190679 A1 | 8/2011 | Humes et al. | |
| 2011/0263022 A1 | 10/2011 | Krause et al. | |
| 2012/0037564 A1 | 2/2012 | Tullis et al. | |
| 2012/0067815 A1 | 3/2012 | Luttropp et al. | |
| 2012/0067821 A1 | 3/2012 | Chang et al. | |
| 2012/0134974 A1 | 5/2012 | Sehgal | |
| 2012/0165176 A1 | 6/2012 | Andou | |
| 2012/0305482 A1 | 12/2012 | McCrea et al. | |
| 2013/0004454 A1 | 1/2013 | Weiss et al. | |
| 2013/0306544 A1 | 11/2013 | Ueno et al. | |
| 2014/0012097 A1 | 1/2014 | McCrea et al. | |
| 2014/0038084 A1 | 2/2014 | Honel et al. | |
| 2014/0166580 A1 | 6/2014 | Rempfer et al. | |
| 2015/0048533 A1 | 2/2015 | Savariar et al. | |
| 2015/0053608 A1 | 2/2015 | Yeager et al. | |
| 2015/0076066 A1 | 3/2015 | Zink et al. | |
| 2015/0111849 A1 | 4/2015 | McCrea et al. | |
| 2015/0114224 A1 | 4/2015 | Liu et al. | |
| 2015/0190563 A1 | 7/2015 | Nakaguma et al. | |
| 2015/0274891 A1 | 10/2015 | Konradi et al. | |
| 2015/0320924 A1 | 11/2015 | Flieg et al. | |
| 2015/0328597 A1 | 11/2015 | McCloskey et al. | |
| 2016/0101229 A1 | 4/2016 | McCrea et al. | |
| 2016/0375230 A1 | 12/2016 | Lee et al. | |
| 2017/0165616 A1 | 6/2017 | Boschetti-De-Fierro et al. | |
| 2019/0106545 A1 | 4/2019 | Russell et al. | |

FOREIGN PATENT DOCUMENTS

| | | |
|---|---|---|
| CN | 105555819 A | 5/2016 |
| DE | 102007027842 A1 | 12/2008 |
| JP | 2004131566 A | 4/2004 |
| WO | 8900589 A1 | 1/1989 |
| WO | 9809582 A1 | 3/1998 |
| WO | 0038758 A1 | 7/2000 |
| WO | 03078023 A1 | 9/2003 |
| WO | 2008100559 A2 | 8/2008 |
| WO | 2011000086 A1 | 1/2011 |
| WO | 2011107517 A1 | 9/2011 |
| WO | 2012127422 A1 | 9/2012 |
| WO | 2013146263 A1 | 10/2013 |
| WO | 2014051537 A1 | 4/2014 |
| WO | 2014079991 A1 | 5/2014 |
| WO | 2014170391 A1 | 10/2014 |

(56) References Cited

FOREIGN PATENT DOCUMENTS

WO      2015091181 A2    6/2015
WO      2016184945 A1    11/2016

OTHER PUBLICATIONS

Baumann et al., "Surface modification of the polymers present in a polysulfone hollow fiber hemodialyser by covalent binding of heparin or endothelial cell surface heparan sulfate: flow characteristics and platelet adhesion," J Biomater Sci Polym Ed., 2000, 11(3), pp. 245-272 (abstract only).

International Search Report and Written Opinion issued in corresponding International Patent Application No. PCT/US2018/053250 dated Jan. 29, 2019 (11 pages).

Office Action issued in corresponding Chinese Patent Application No. 201880059529.7 dated Aug. 10, 2021 (with English translation)(31 pages).

* cited by examiner

FIG. 1

Scheme 1

(1a)  $D + G \longrightarrow D\text{-}G\text{-}D$ (2a)  $D\text{-}G\text{-}D + D + {}_{xs}E \longrightarrow E\text{-}(D\text{-}E)_{x1}\text{-}(D\text{-}G\text{-}D)_{y1}\text{-}(E\text{-}D)_{x2}\text{-}E$ x1=1-100, e.g.,10-100, y1=1-100, e.g., 1-10, x2=1-100, e.g.,10-100

Scheme 2

(1b)  ${}_{xs}D + E \longrightarrow D\text{-}(D\text{-}E)_{x3}\text{-}D + D$ (2b)  $G + D + D\text{-}(D\text{-}E)_{x3}\text{-}D \longrightarrow [D\text{-}(E\text{-}D)_{x4}\text{-}(G)_{m3}\text{-}(D\text{-}E)_{x5}]_{x9}\text{-}D$ x3=1-100, e.g., 10-30, x4=1-100, e.g., 10-30, m3=1-100, e.g., 1-10,
x5=1-100, e.g.,10-30, x9=1-100, e.g., 1-10

Scheme 3

(1c)  $D + {}_{xs}E \longrightarrow E\text{-}(D\text{-}E)_{x6}\text{-}D\text{-}E$ (2c)  $D + G \longrightarrow D\text{-}G\text{-}D$ (3c)  $E\text{-}(D\text{-}E)_{x6}\text{-}D\text{-}E + D\text{-}G\text{-}D \longrightarrow E\text{-}(D\text{-}E)_{x7}\text{-}D\text{-}E\text{-}(D\text{-}G\text{-}D)_{m4}\text{-}(E\text{-}D)_{x8}\text{-}D\text{-}E$ x6= 1-100, e.g.,10-30, x7=1-100, e.g., 10-30,
m4=1-100, e.g., 1-10, x8=1-100, e.g., 10-30

$m_1$= 1-10, $m_2$= 0-10
Urethane Block/Oligomer (G)

POLYSULFONE-URETHANE COPOLYMER, MEMBRANES AND PRODUCTS INCORPORATING SAME, AND METHODS FOR MAKING AND USING SAME

This application is a continuation of U.S. patent application Ser. No. 16/145,225, filed Sep. 28, 2018, which in turn claims the benefit under 35 U. S.C. § 119(e) of prior U.S. Provisional Patent Application No. 62/568,556, filed Oct. 5, 2017, which is incorporated in its entirety by reference herein.

BACKGROUND OF THE INVENTION

The present invention relates to polysulfone-urethane copolymers and processes for making them, membranes and products incorporating them, processes of making the membranes, and uses of membranes and products including them.

Membranes which have selective permeabilities are widely used in various products, such as filtration media used in the medical field. Membranes having a form of hollow fiber are particularly suitable for the preparation of high area per volume membranes, such as hollow fiber membranes suitable for hemodialysis, hemofiltration, or hemodiafiltration. A variety of polymers, including polysulfone, polyethersulfone, cellulose, cellulose acetate, polyamides, polyacrylonitriles, polymethyl methacrylates, polyvinyl alcohols, polyolefins, and the like, have been used to form such hollow fiber membranes.

Pore forming additives (e.g., polyvinylpyrrolidone (PVP), polyethylene glycol (PEG)) are generally added to membrane-forming polymers with hydrophobic characteristics (e.g., polysulfone (PSF), polyethersulfone (PES)) for fabrication of microporous membranes using a wet phase inversion process. In addition to facilitating the formation of porous or microporous structures during membrane fabrication, pore forming additives can enhance hydrophilicity and/or blood compatibility of the membranes. However, the pore forming additives can be leached out of the membrane core and the membrane's active surface during membrane fabrication as well as in membrane applications involving aqueous-based fluid. These applications can include, for instance, kidney dialysis, blood oxygenation, blood separation, water purification (or treatment), dairy processing, and separations in the biotechnology and pharmaceutical industry. When additives are leached out of the membrane's active surface, the membrane surface can be prone to negative artifacts, such as membrane fouling and poor blood compatibility.

A need exists for improved membrane materials which can act as pore forming agents with reduced risk of leaching out of the membranes while enhancing blood compatibility.

SUMMARY OF THE PRESENT INVENTION

A feature of the present invention is to provide a copolymer which can be a membrane component or other product component, which meets the above and/or other needs.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a polysulfone-urethane copolymer comprising formula (I) or formula (II):

wherein G is a urethane block, D is a divalent residue of an aromatic dihydroxyl compound, and E is an aromatic sulfone group, wherein i) a1, a2 and a3 are independently from 1-100 which randomly or non-randomly repeat in formula (I), and ii) b 1, b2, b3, and b4 are independently from 1-100 which randomly or non-randomly repeat in formula (II).

The present invention further relates to a polymer composition comprising the indicated polysulfone-urethane copolymer in an amount of from about 10% to about 100% by weight, based on total weight of the polymer composition.

The present invention further relates to a membrane comprising the indicated polysulfone-urethane copolymer.

The present invention further relates to a method for preparing the indicated polysulfone-urethane copolymer, comprising 1) reacting at least one oligo- or polyurethane block with an aromatic dihydroxyl compound which end caps the at least one oligo- or polyurethane block to form an end-capped oligo- or polyurethane block, and 2) reacting the end-capped oligo- or polyurethane block with an aromatic diol and a dihalodiphenyl sulfone to form a polysulfone-urethane copolymer with control of stoichiometry so that the polysulfone-urethane copolymer has dihalodiphenyl sulfone end groups.

The present invention further relates to a method for preparing the indicated polysulfone-urethane copolymer, comprising 1) reacting an aromatic diol and a dihalodiphenyl sulfone to form a polysulfone block, and control the stoichiometry so that the polysulfone block is end-capped with residue of an aromatic diol, and 2) reacting at least one oligo- or polyurethane block, an aromatic dihydroxyl compound, and the polysulfone block to form a polysulfone-urethane copolymer.

The present invention further relates to a method for preparing the indicated polysulfone-urethane copolymer, comprising 1) reacting aromatic diol and a dihalodiphenyl sulfone to form a polysulfone block, and control the stoichiometry so that the polysulfone block has dihalodiphenyl end groups, 2) reacting at least one oligo- or polyurethane block with an aromatic dihydroxyl compound which end caps the at least one oligo- or polyurethane block, and 3) reacting the sulfone block and the end-capped oligo- or polyurethane block to form a polysulfone-urethane copolymer.

The present invention further relates to a process of making a membrane comprising preparing a dope solution containing the indicated polysulfone-urethane copolymer, and forming a hollow fiber or flat sheet with the dope solution.

The present invention further relates to a process of making a membrane, comprising a) forming a spinning mass comprising the indicated polysulfone-urethane copolymer, and b) spinning the spinning mass through a spinneret to form hollow fibers.

The present invention further relates to a dialyzer comprising the indicated hollow fibers.

The present invention further relates to a process for hemodialysis or hemofiltration or hemodiafiltration comprising contacting blood with a membrane comprising at least one of the indicated hollow fibers or flat sheet.

It is to be understood that both the foregoing general description and the following detailed description are exemplary and explanatory only and intended to provide a further explanation of the present invention, as claimed.

BRIEF DESCRIPTION OF DRAWINGS

FIG. 1 is a process flow diagram of a method of production of a polysulfone-urethane copolymers according to Schemes 1, 2 or 3, according to examples of the present application.

DETAILED DESCRIPTION OF THE PRESENT INVENTION

Figure 2:
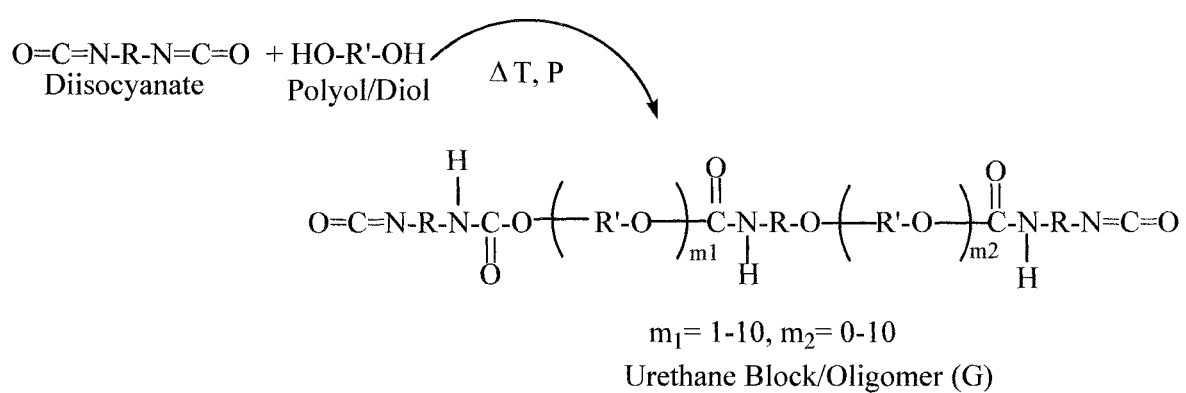
FIG. 2 shows a reaction scheme for synthesizing a polyurethane block/oligomer intermediate which can be used in synthesizing a polysulfone-urethane copolymer of the present invention, according to an example of the present application.

Polysulfone-polyurethane copolymers are disclosed which are suitable for medical products, such as membranes for dialysis, filtration, or other solute and/or solvent exchange processes, or other products. These polysulfone-polyurethane copolymers can be used to supplant more highly leachable pore-forming additives, such as polyvinyl pyrrolidone (PVP) or polyethylene glycol (PEG), at least in part or entirely, in membranes or other products. This can reduce risk of additive leaching out of such products.

Additionally or alternatively, these polysulfone-polyurethane copolymers can be used as polymer matrix material in the membranes or other products, as the only polymer matrix material or in combination with other polymer matrix material. Membranes incorporating these polysulfone-polyurethane copolymers can be used for dialysis or other applications where the membrane is in contact with blood or other body fluid.

Membranes incorporating these polysulfone-polyurethane copolymers can have comparable or greater blood compatibility or other enhanced properties compared to membranes formed with a typical polyarylethersulfone and PVP additive.

The polysulfone-polyurethane copolymers according to the present invention can be used in methods which provide a solution that can be formed into articles, such as cast, spun, extruded or molded medical articles (e.g., hollow fiber or flat sheet membranes), which can have the desired low leach out, blood compatibility, and/or other desirable properties.

Methods are provided for synthesizing the polysulfone-polyurethane copolymers which, as an option, use multi-stage reactions which involve reactions of urethane oligomer, aromatic dihydroxyl compounds, and dihalodiphenyl sulfone in combinations and under conditions controlled to form block copolymers of polyurethane and polysulfone.

As an option, polysulfone-urethane copolymer according to this invention can comprise formula (I) or formula (II):

   (I)

   (II)

wherein G is a urethane block, D is a divalent residue of an aromatic dihydroxyl compound, E is an aromatic sulfone group, and wherein i) a1, a2 and a3 are independently from 1-100 which randomly or non-randomly repeat in formula (I), and ii) b1, b2, b3, and b4 are independently from 1-100 which randomly or non-randomly repeat in formula (II). As an option, E can be a di-reacted residue of a dihalodiphenyl sulfone, D can be di-reacted residue of a dihydroxybiphenyl or a dihydroxydiphenyl sulfone, and G can comprise an oligo- or polyurethane chain. Further examples of G, D, and E are included herein.

As an option, the polysulfone-urethane copolymer can comprise formula (I):

wherein a1 and a3 are independently from 10-100 and a2 is from 1-10 units which randomly or non-randomly repeat in formula (I); or formula (II):

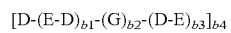

wherein b1 and b3 are independently from 10-100 and b2 and b4 are independently from 1-10 units which randomly or non-randomly repeat in formula (II).

The urethane block/oligomer G can comprise the reaction product of polyol (e.g., diol) and diisocyanate. As an option, G can have a structure of formula (IV):

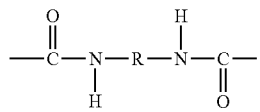 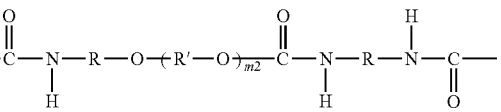

wherein R is a divalent residue of an aliphatic or aromatic diisocyanate linker, R' is a divalent residue of an organic polyol compound which is different from D, m1 is 1-10, and m2 is 0-10. As an option, G can further comprise at least one amphiphilic or hydrophilic or hydrophobic block in the oligo- or polyurethane chain. As an option, the blood compatibility of the polysulfone-polyurethane copolymer which incorporates the polyurethane chain can be enhanced by incorporating amphiphilic or hydrophilic or hydrophobic blocks in the polyurethane chain, or modifying at least one of the terminal groups of the oligo- or polyurethane chain, or a combination thereof. For purposes herein, a polymer, oligomer, membrane (hollow or flat), or other material that is "hydrophilic" has a strong affinity for water or can be wetted with water. A polymer, oligomer, membrane, or other material that is "hydrophobic" lacks or has little affinity for water or is nonwettable with water. A polymer, oligomer, membrane, or other material that is "amphiphilic" possesses both hydrophilic and hydrophobic properties.

As an option, D can have formula (V):

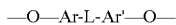

wherein each of Ar and Ar' is an aromatic moiety; L is a linking moiety selected from $L^1$ or $L^2$, wherein $L^1$ has the formula (VI):

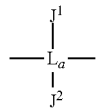

wherein $L_a$ is alkyl or alkylarylalkyl (or alkylaralkyl), and each of $J^1$ and $J^2$ is independently selected from hydrogen, alkyl, halogenated alkyl, halogenated arylalkyl, alkenyl, haloalkenyl, phenyl, halogen, hydroxyalkyl, hydroxyarylalkyl, alkynyl, alkyloxy, arylalkyloxy, aminoalkyl, aminoarylalkyl, alkyl and arylalkyl substituted by carboxylic acid, ester, amide, aldehyde and ketone function, and $L^2$ is $SO_2$.

As an option, E can have formula (VII):

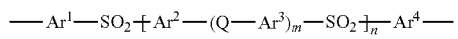

wherein each of m and n are independently zero or an integer of 1 to 10; each of $Ar^1$, $Ar^2$, $Ar^3$ and $Ar^4$ is an unsubstituted or substituted aromatic moiety; Q is a bond or a divalent group. In formula (VII), "$SO_2$" refers to a sulfonyl linkage. As an option, one or more of $A^1$, $Ar^2$, $Ar^3$ and $Ar^4$ may be a substituted aromatic moiety comprising at least one substituent selected from halogen, alkyl, haloalkyl, alkenyl, aryl, ether, carboxyl, ester, amino, amide, imide, and quaternary amine, or other substituents. As an option, Q is a bond, unsubstituted or substituted phenyl, —$CH_2$—, —C(O), —$C(CH_3)_2$—, —$C(CF_3)_2$—, —C(=$CCl_2$), —$C(CH_3)(CH_2CH_2COOH)$—, wherein Q is a bond, unsubstituted or substituted phenyl, —$CH_2$—, —C(O), —$C(CH_3)_2$—, —$C(CF_3)_2$—, —C(=$CCl_2$), or —$C(CH_3)(CH_2CH_2COOH)$—.

As an option, D and E can be residues obtained from condensing reactants such as shown in formulas (V) and (VII) in the resulting copolymeric structures. As an option, D can be derived as a residue of a reactant which can be bisphenol A (IUPAC name: 4,4'-(propane-2,2-diyl)diphenol) (also commonly referred to as "BPA"), bisphenol B (4,4'-(butane-2,2-diyl)diphenol), bisphenol C (4,4'-isopropylidenedi-o-cresol), bisphenol E (4,4'-ethylidenebisphenol), bisphenol F (4,4'-methylenediphenol), bisphenol S (4,4'-sulfonyldiphenol), bisphenol Z (4,4'-cyclohexylidenebisphenol), bisphenol AF (2,2-bis(4-hydroxyphenyl)hexafluoropropane), bisphenol BP (4,4'-(diphenylmethylene)diphenol), or others. As an option, E can be derived as a residue from a reactant that can be an aromatic dihalosulfone compound, such as a dihalodiphenyl sulfone, e.g., dichlorodiphenyl sulfone, difluorodiphenyl sulfone, and dibromodiphenyl sulfone, or others. As a preferred option, E can be derived from a reactant which can be a 4,4'-dihalodiphenyl sulfone, such as 4,4'-dichlorodiphenyl sulfone (DCDPS), 4,4'-difluorodiphenyl sulfone, and 4,4'-dibromodiphenyl sulfone.

As an option, the polysulfone-urethane copolymer can comprise formula (III):

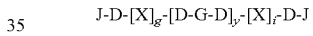

wherein J is an end group of the polymer, X is a polysulfone block comprised of aromatic dihydroxyl compound and dihalodiphenyl sulfone, wherein g and i are independently from 1-100 units. As an option, each J is a mono-reacted residue of a dihalodiphenyl sulfone or a polysulfone block containing an aromatic dihydroxyl compound and a dihalodiphenyl sulfone end unit, and each of D and G are as described earlier.

As an option, the polysulfone block of a polysulfone-polyurethane copolymer of the present invention may be derivatized. As an option, the polysulfone-polyurethane copolymers can be subjected to post-polymerization modifications to add functional groups (e.g., chloromethyl or quaternary amines) to the aromatic rings of the polysulfone units of the copolymer backbone to modify surface properties for improved wetting, biocompatibility, solubility, or any combination thereof. These polysulfone-polyurethane copolymers can provide an alternative to typical surface modifying macromolecules (SMMs) (e.g., SMMs having halogenated end groups as surface active groups) in use in medical products.

As an option, the polysulfone-urethane copolymer according to the invention can have a weight average molecular weight of from about 10,000 to about 750,000 g/mol, or from about 25,000 to about 600,000 g/mol, or from about 50,000 to about 500,000 g/mol, or from about 75,000 to about 350,000 g/mol, or from about 100,000 to about 250,000 g/mol, or other values.

As an option, any one of three general reaction schemes can be used for synthesizing polysulfone-polyurethane copolymers according to the invention. These general reaction schemes are shown in FIG. 2 as Schemes 1, 2, and 3.

The first reaction scheme shown as Scheme 1 in FIG. 1 comprises two reaction steps (1a) and (2a). In first step (1a) of Scheme 1, urethane block/oligomer (abbreviated as "G" herein) can be end-capped with aromatic dihydroxyl compound (abbreviated as "D" herein) to form an end-capped urethane oligomer (abbreviated "D-G-D" herein), and then, in second step (2a), the end-capped urethane oligomer D-G-D can be added to a polysulfone polymerization reaction wherein the end-capped oligomer D-G-D can be reacted with aromatic dihydroxyl compound (D) and dihalodiphenyl sulfone compound (abbreviated as "E" herein) with the stoichiometry controlled to form block copolymer of polyurethane and polysulfone having dihalodiphenyl sulfone compound (E) end groups.

Figure 3:
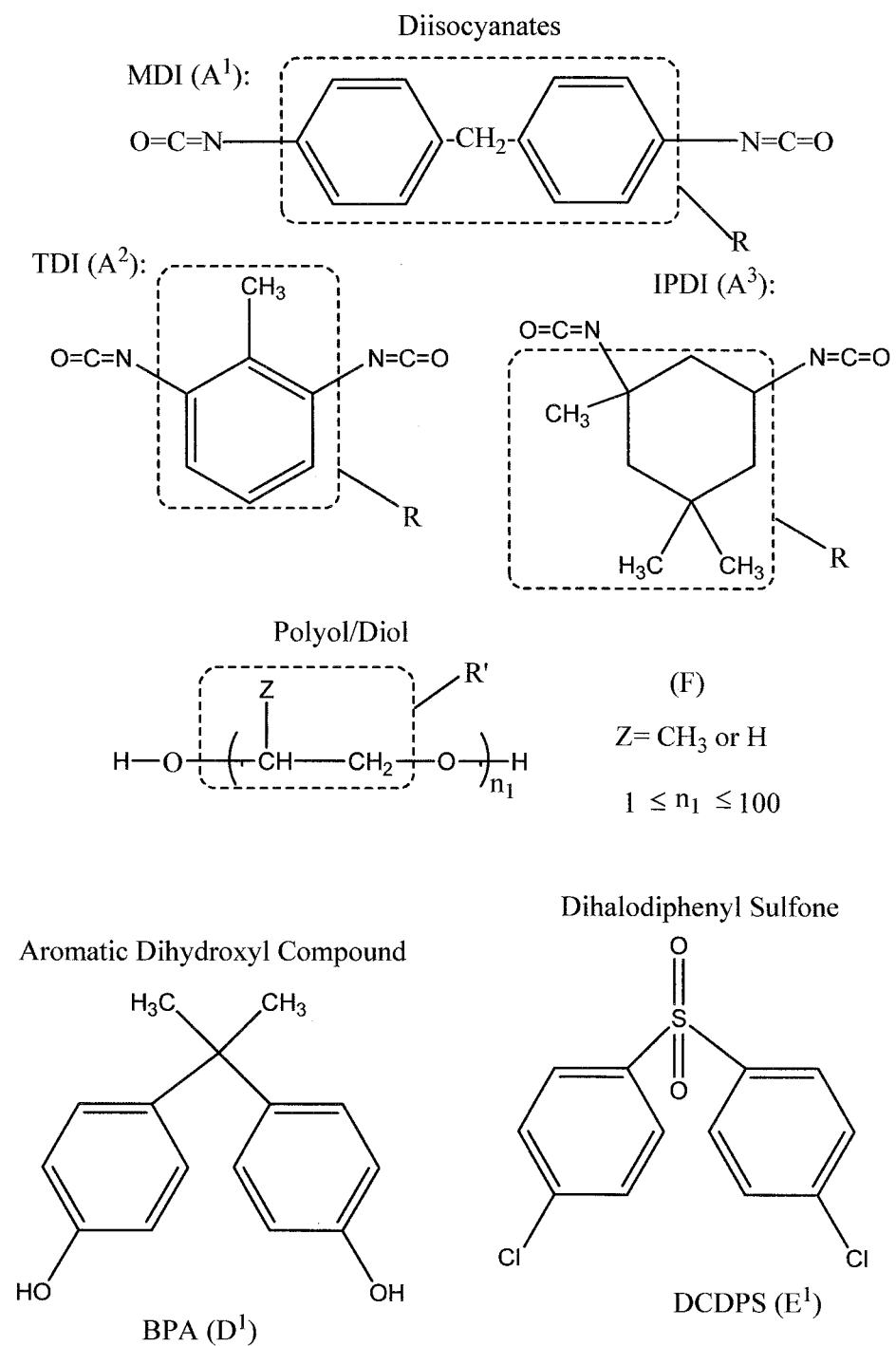
FIG. 3 shows examples of a diisocyanate, a polyol, an aromatic dihydroxyl compound, and a dihalodiphenyl sulfone, which can be used as reactants in the methods of Schemes 1, 2, and 3 of FIG. 1 in the production of polysulfone-urethane copolymers of the present invention, according to examples of the present application.
Figure 4:
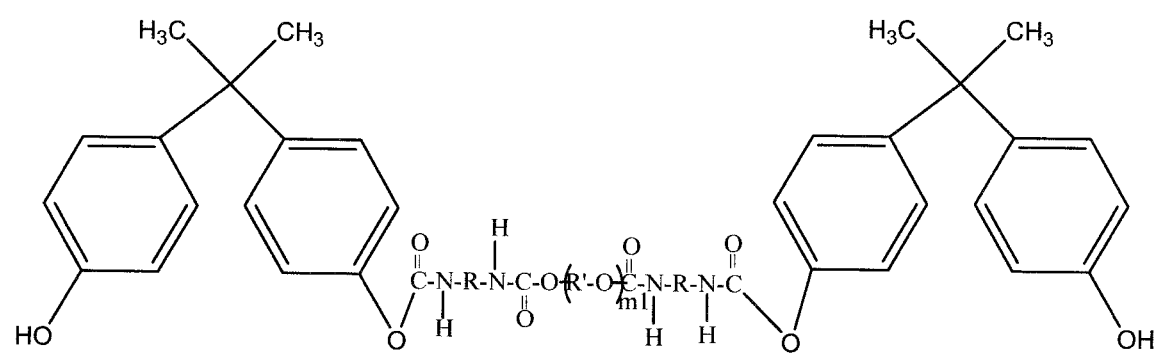
FIG. 4 shows a bisphenol-A end-capped urethane oligomer of FIG. 2, which can be formed as an intermediate product in reaction steps of Schemes 1 and 3 shown in FIG. 1, in the production of a polysulfone-urethane copolymer according to those reaction schemes, according to an example of the present application.

In Step (1a) of Scheme 1, the urethane oligomer end-capping can be provided by reaction of isocyanate (NCO) end groups of diisocyanate with bisphenol or other aromatic dihydroxyl compound in an organic solvent, e.g., a polar aprotic solvent. The bisphenol or other aromatic dihydroxyl compound may be used in a stoichiometric amount or stoichiometric excess. The urethane oligomer (G) used in this reaction step (1a) of Scheme 1, and in step (2b) of Scheme 2 discussed herein, can be synthesized or commercially obtained. FIG. 2, for example, shows a general reaction scheme which can be used, as an option, for making urethane oligomers from diisocyanate and polyol, which can be used in methods of the present invention. Conventional methods for synthesizing urethane oligomers can be used, as an option, such as those shown in U.S. Pat. No. 8,071,683, which is incorporated in its entirety by reference herein. Alternatively, as indicated, the urethane oligomers may be commercially obtained. FIG. 3 shows examples, as options, for diisocyanates (abbreviated as "$A^1$", "$A^2$", "$A^3$") which can be used as the diisocyanate, and a general structure (abbreviated as "F") which encompasses diols/polyols which can be used, in the reactions of FIG. 2. The moieties R and R' identified in FIG. 3 provide examples of similarly identified groups in the urethane oligomer structure shown in FIG. 2. FIG. 3 also shows, bisphenol A (abbreviated "$D^1$") which can be used, as an option, for compound D is steps (1a) and (2a) of Scheme 1. Further, referring to FIG. 4, an example of the end-capped urethane oligomer (D-G-D) is shown where the end groups (D) are monovalent residues of bisphenol A and the intermediate chain is shown as divalent residue of the urethane oligomer shown in FIG. 2, as an option, where m2 is made zero to simplify the illustration. Referring to the bisphenol-A end-capped urethane oligomer shown in FIG. 4, R can be diisocyanate moieties such as any of those identified in FIG. 3, and R' can be a divalent residue of a polyol, such as R' derived from the "Polyol/Diol" (F) shown in FIG. 3.

To prepare the aromatic dihydroxyl end-capped urethane oligomer intermediate such as shown in step (1a) of Scheme 1, as an option, the reactants can be combined in a reactor vessel and maintained at a reaction temperature of 65° C.±5° C. at atmospheric pressure (e.g., about 1013.25 mbar) for a minimum of at least about 2 hours or until no change was seen in the amount of NCO end groups (e.g., by NCO titration). The resulting product can be cooled and then stored at ambient conditions until used in the step of synthesizing the polysulfone-urethane copolymer.

Figure 5:
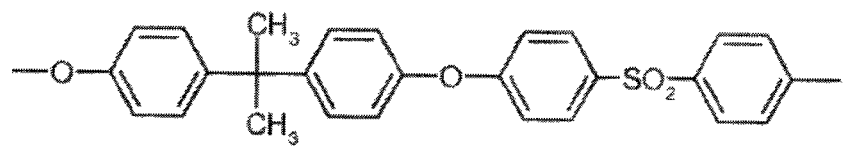
FIG. 5 shows a repeating unit of a polysulfone-urethane copolymer comprising bisphenol A (BPA) and 4,4'-chlorodiphenyl sulfone (DCDPS), according to an example of the present application.

In step (2a) of Scheme 1, the end-capped polyurethane oligomer (D-G-D) produced in step (1a) can be reacted with an aromatic diol (D) (e.g., an aromatic dihydroxyl compound) and a dihalodiphenyl sulfone (E) to form a polysulfone-urethane copolymer with control of stoichiometry so that the polysulfone-urethane copolymer has dihalodiphenyl sulfone (E) end groups, and includes the -D-E-, -D-G-D-, and -E-D-units shown in step (2a), which can be present in values indicated for x1, y1, and x2, respectively, in the figure. FIG. 3 shows 4,4'-dichlorodiphenyl sulfone (abbreviated "$E^1$") which can be used, as an option, for compound E in step (2a) of Scheme 1. FIG. 5 shows an illustration of a -D-E-repeating unit shown in the polysulfone-urethane copolymer product which, as an option, can be comprised of bisphenol A (BPA) and 4,4'-chlorodiphenyl sulfone (DCDPS). The reaction in Step (2a) of Scheme 1 can be performed in the presence of at least one metal carbonate (e.g., dipotassium carbonate) and organic solvent, e.g., a polar aprotic solvent, with the dihalodiphenyl sulfone (D) used in stoichiometric excess. While not desiring to be bound to a particular theory, the at least one metal carbonate may be a deprotonating base with respect to the aromatic diol (aromatic dihydroxyl compound) to support a polycondensation reaction in the reaction mixture.

To prepare a polysulfone-urethane copolymer according to the present invention using the aromatic dihydroxyl end-capped urethane oligomer solution obtained in step (1a) with aromatic dihydroxyl compound and stoichiometric excess ("XS") of dihalodiphenyl sulfone, such as shown in step (2a) of Scheme 1, as an option, the reaction mixture can be reacted in the presence of the metal carbonate as a catalyst at a reaction temperature of from about 145° C. to about 160° C. (e.g., about 152° C. to 155° C.) in a reaction vessel setup with inter alia a fractionation column (e.g., Dean-Stark trap and water-cooled condenser). Under these reaction conditions and set-up, the aromatic dihydroxyl end-capped urethane oligomer can form a phenolate salt anion, which competes with the free aromatic dihydroxyl compound for the dihalodiphenyl sulfone, and this allows the urethane blocks to be incorporated into the polysulfone chain. Byproduct water is removed during the reaction, and the progress of the reaction can be monitored using gel permeation chromatography and torque as indicators for polymerization progress. Molecular weight of the copolymer product can be a positive function of the duration of the reaction. For example, for a reaction of BPA-end-capped PPG-TDI urethane, BPA, and DCDPS under the indicated reaction conditions, the molecular weight (Mw) of the polysulfone-urethane copolymer product may be about 15,000 to about 25,000 Daltons after about 18 hours, about 65,000 to about 75,000 Daltons after about 38 hours, and about 70,000 to about 85,000 after about 45 hours, or other values. In view of this, the duration of the reaction may be at least 10 hours, or at least 20 hours, or at least 30 hours, or at least 40 hours, or other times, such as depending on the selections for the reactants and reaction conditions.

The isolation of a polysulfone-urethane copolymer product obtained according to the present invention may be carried out, for example, by filtering the reaction solution and then precipitating the polymer by adding the polymer solution to water, and blending them with agitation to remove most of solvent and to precipitate the copolymer. Low molecular weight species, such as oligomer (e.g., unreacted oligomer), may be present with the polysulfone-urethane copolymer product in the reaction solution. The low molecular weight species can be separated from the polysulfone-urethane copolymer product by the isolation procedure to purify the copolymer product. Low molecular weight species can have molecular weights 1.5 kDa or lower, or from about 0.3 kDa to about 1.5 kDa. The copolymer can be ground into powder by the blender, then vacuum filtered and washed with fresh water again with agitation, and this process can be repeated one or more times, after which the isolated copolymer can be dried (e.g., oven dried at about 120° C. for about 12 hours) to provide a polysulfone-urethane copolymer product in powder form. The polysulfone-urethane copolymer can be isolated as a dry solid which remains as solid at about 25° C. The solid form can be dissolvable in an organic solvent. The solid form of the additive may be a solid particulate (e.g., powder, pellets, or other flowable dry solid particles), or a solid thin film.

The second reaction scheme shown as Scheme 2 in FIG. 1 comprises two reaction steps (1b) and (2b). In first step (1b) of Scheme 2, aromatic dihydroxyl compound (D) can be reacted with dihalodiphenyl sulfone compound (E) with the stoichiometry controlled to produce polysulfone blocks (abbreviated as "D-(E-D)$_{x3}$-D" in Scheme 2 having aromatic dihydroxyl compound (D) end groups, and allowing a slight excess of unreacted aromatic dihydroxyl compound (D), and then, in step (2b) urethane oligomer (G), aromatic dihydroxyl compound (D), and the sulfone block (D-(E-D)$_{x3}$-D) produced in step (1b) of Scheme 2 can be reacted to form a polysulfone-urethane block copolymer.

In step (1b) of Scheme 2, aromatic dihydroxyl compound (D) can be reacted with dihalodiphenyl sulfone (E), with compound (D) in stoichiometric excess ("XS"), to produce the polysulfone blocks (D-(E-D)$_{x3}$-D) that have aromatic dihydroxyl compound end groups, and, as indicated, allowing for a slight excess of unreacted aromatic dihydroxyl compound (D). The -D-E-units can be present in values indicated for x3 in the figure. The reaction in Step (1b) of Scheme 2 can be performed in the presence of at least one metal carbonate (e.g., dipotassium carbonate) and solvent, e.g., a polar aprotic solvent.

To prepare the aromatic dihydroxyl end-capped repeating unit comprised of aromatic dihydroxyl compound and dihalodiphenyl sulfone such as shown in step (1b) of Scheme 2, the reaction mixture can be reacted in the presence of the metal carbonate as catalyst at a reaction temperature of from about 145° C. to about 185° C. for about 2 hours to about 12 hours in a reaction vessel setup with inter alia a fractionation column (e.g., Dean-Stark trap and water-cooled condenser).

In step (2b) of Scheme 2, urethane oligomer (G) and dihydroxyl compound (D) can be reacted with the polysulfone blocks (D-(E-D)$_{x3}$-D) produced in step (1b) to form a polysulfone-urethane block copolymer. The -D-E-, -E-D-, -G-, -D-E-, and D-(E-D)$_{x4}$-(G)$_{m3}$-(D-E)$_{x5}$, units shown in step (2b) can be present in values indicated for x3, x4, m3, x5, and x9, respectively, in the figure. The reacted mixture may have small amounts of end-capped urethane oligomer (D-G-D) (not shown) which, if present, can be removed by ultrafiltration. The reaction in Step (2b) of Scheme 2 can be performed in the presence of at least one metal carbonate (e.g., dipotassium carbonate) and solvent, e.g., a polar aprotic solvent.

The intermediate oligomer product solution of step (1b) can be reacted in step (2b) with urethane oligomer and aromatic dihydroxyl compound in the presence of the metal carbonate as catalyst at a reaction temperature of from about 145° C. to about 185° C. for about 2 hours to about 12 hours in a similar reaction vessel setup with a fractionation column to produce the polysulfone-urethane copolymer product. This copolymer product of Scheme 2 can be isolated in a similar manner as indicated for Scheme 1.

The third reaction scheme shown as Scheme 3 in FIG. 1 comprises three reaction steps (1c), (2c), and (3c). In first step (1c), aromatic dihydroxyl compound (D) is reacted with dihalodiphenyl sulfone compound (E) with the stoichiometry controlled to produce polysulfone blocks (abbreviated as "E-(D-E)$_{x6}$-D-E" in Scheme 3) having dihalodiphenyl sulfone (E) end groups, and in a second step (2c), an urethane block/oligomer (G) is end-capped with aromatic dihydroxyl compound (D) to form end-capped urethane oligomer (D-G-D), and then, in a third step (3c), the polysulfone block (E-(D-E)$_{x6}$-D-E) formed in step (1) can be reacted with the end-capped urethane oligomer D-G-D produced in step (2c) to create a polysulfone-urethane block copolymer structure.

In step (1c) of Scheme 3, aromatic dihydroxyl compound (D) can be reacted with dihalodiphenyl sulfone (E), with compound (E) in stoichiometric excess ("XS"), to produce polysulfone blocks (E-(D-E)$_{x6}$-D-E) that have dihalodiphenyl sulfone end groups. The -D-E-units shown in step (1c) can be present in values indicated for x6 in the figure. The reaction in step (1c) of Scheme 3 can be performed in the presence of at least one metal carbonate (e.g., dipotassium carbonate) and solvent, e.g., a polar aprotic solvent.

To prepare the intermediate oligomer product such as shown in step (1c) of Scheme 3 which comprises repeating units of aromatic dihydroxyl compound and dihalodiphenyl sulfone and dihalodiphenyl sulfone end groups, as an option, the reaction mixture can be reacted in the presence of the metal carbonate as catalyst at a reaction temperature of from about 145° C. to about 185° C. for about 2 hours to about 12 hours in a reaction vessel setup with inter alia a fractionation column (e.g., Dean-Stark trap and water-cooled condenser).

In step (2c) of Scheme 3, the urethane oligomer end-capping with an aromatic dihydroxyl compound can be achieved by use of a similar reaction and conditions as indicated for step (1a) of Scheme 1.

In step (3c), polysulfone blocks (E-(D-E)$_{x6}$-D-E) produced in step (1c) can be reacted with the end-capped polyurethane oligomer (D-G-D) of step (2c) to form a polysulfone-urethane copolymer. The -D-E-, -D-E-, -D-G-D-, and -E-D-, units shown in step (3c) can be present in values indicated for x6, x7, m4, and x8, respectively, in the figure. The reaction in step (3c) of Scheme 3 can be performed in the presence of at least one metal carbonate (e.g., dipotassium carbonate) and solvent, e.g., a polar aprotic solvent.

For step (3c) of Scheme 3, the intermediate oligomer product solution obtained from step (1c) can be reacted with the aromatic dihydroxyl end-capped urethane oligomer obtained from step (2c) in the presence of the metal carbonate as catalyst at a reaction temperature of from about 145° C. to about 185° C. for about 2 hours to about 12 hours in a similar reaction vessel setup with a fractionation column to produce the polysulfone-urethane copolymer product. This copolymer product can be isolated in a similar manner as indicated for Scheme 1.

For purposes of any individual reaction steps or stages of Schemes 1, 2, and 3, the components of the respective reaction mixture can be generally reacted concurrently. The individual components may be mixed in an upstream step and subsequently be reacted. It is also possible to feed the individual components into a reactor in which these are mixed and are then reacted, wherein the individual components may be simultaneously fed into the reactor, or one or more of the reactants can be prefed into the reactor and the remaining reactant(s) can be dosed into the reaction mixture during the reaction.

As an option, the organic solvent, (e.g., polar aprotic solvent) indicated as used in various steps of Schemes 1, 2 and 3 can be at least one of dimethylacetamide (DMAC), dimethylformamide (DMF), tetrahydrofuran (THF), N-methylpyrrolidone (NMP), N-ethyl-2-pyrrolidone (NEP), dimethylsulfoxide (DMSO), tetrahydrofuran (THF), N-ethylpyrrolidone (NEP), N-octylpyrrolidone, dimethylformamide (DMF), butyrolactone, sulfolane, anisole, or others. Water of reaction is formed in the condensation reactions, such as between aromatic dihydroxyl compound (D) (e.g., BPA) and dihalodiphenyl sulfone compound (E) (e.g., DCDPS), and in other condensation reactions that may form part of some of the indicated steps of Schemes 1, 2, and 3. Byproduct water can be removed from the reaction mixture, such as by distillation. The metal carbonate indicated for use in some of the reaction steps of Schemes 1, 2 and 3 can be anhydrous. As an option, the metal carbonate can be an alkali metal carbonate, alkaline earth metal carbonate, or any combination thereof. As an option, the metal carbonate can be sodium carbonate, potassium carbonate, and/or calcium carbonate, and preferably can be potassium carbonate. As an option, the metal carbonate can be used in dry fine particle form.

As an option, a polymer composition can be provided which comprises polysulfone-urethane copolymer according to this invention in an amount of from about 1% to about 100%, or from about 10% to about 100%, or from about 15% to about 99 w %, or from about 20% to about 95%, or from about 25% to about 90%, or from about 30% to about 80%, or from about 35% to about 75%, by weight, based on total weight of the composition. As an option, other components of such polymer compositions may be one or more of a different polymer or polymers, solvent(s), additives, or other materials which are chemically co-stable with the polysulfone-urethane copolymer at typical room and storage conditions.

The polysulfone-urethane copolymers according to the invention resulting can be used in the fabrication of medical products, such as dialysis membranes, hemofiltration membranes, diafiltration membranes, or other products. A microporous membrane which incorporates the polysulfone-urethane copolymer can be produced by a method of the present invention, which can have a shape of a hollow fiber, or a flat sheet membrane, or other self-supporting shapes. As an option, the polysulfone-urethane copolymer can be incorporated into polymer dope solutions, which can be mixed, filtered, and spun into hollow fibers, or cast into a film, with contact made with a precipitation fluid, and further processed to form a microporous membrane.

Figure 6:
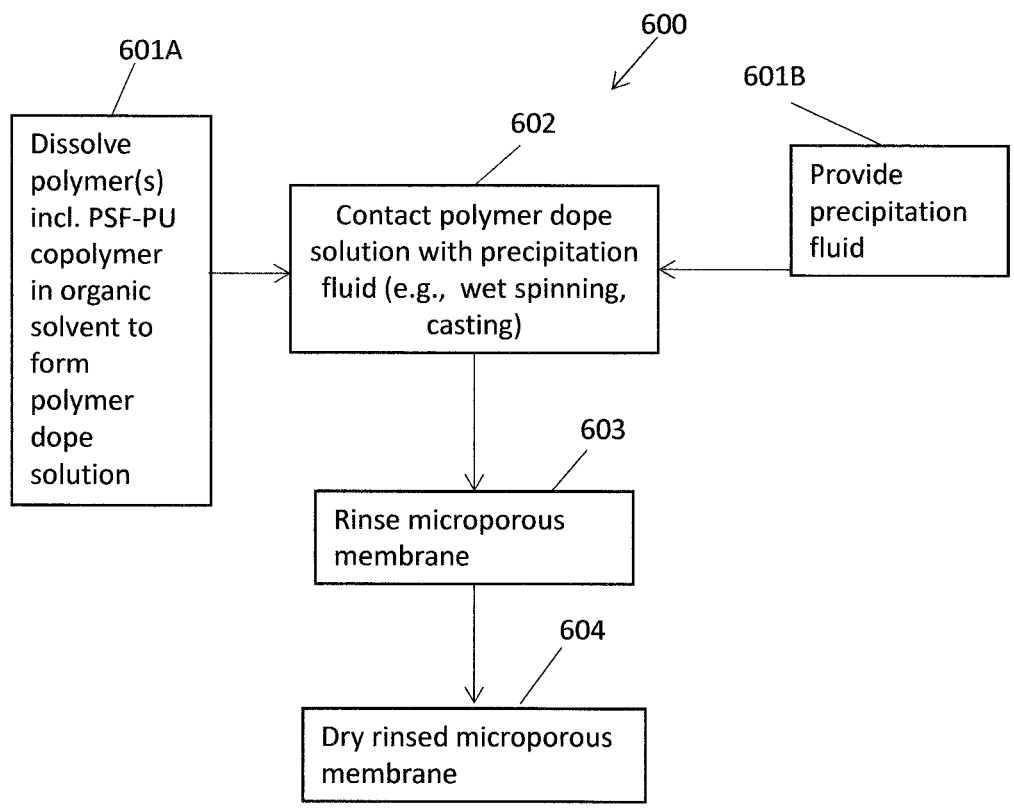
FIG. 6 is a process flow diagram of a method of production of a microporous membrane which incorporates a polysulfone-urethane copolymer, according to an example of the present application.

Referring to FIG. 6, a method of forming a microporous membrane according to an example of the present application, indicated by the identifier 600, includes steps 601A, 601B, 602, 603, and 604. In step 601A, the polymer dope solution is formed by dissolving membrane-forming polymer or polymers, which include membrane matrix-forming polymer and pore forming polymer, in organic solvent. As an option, the polysulfone-urethane copolymer according to the present invention can be used as a matrix polymer, pore forming agent, or both in the membrane. In step 601B, precipitation fluid is provided. The contacting of the polymer dope solution with precipitation fluid in step 602, is followed by rinsing of the membrane in step 603, and drying the rinsed membrane in step 604.

The polymer dope solution can comprise a mixture of at least one polymer which comprises the polysulfone-urethane copolymer according to the present invention and at least one organic solvent that can dissolve the polymer(s). As indicated, the polysulfone-urethane copolymer of the present invention can function as a membrane-forming polymer, a pore-forming agent in the membrane, or both. The mixture of polymer(s) and organic solvent, as a preferred option, can be a homogenous mixture.

In an option, the polysulfone-urethane copolymer is the only membrane-forming polymer used in the membrane. In an option, at least one polymer different from the polysulfone-urethane copolymer is also used as a membrane-forming polymer in combination with the polysulfone-urethane copolymer. If used, the different polymer used as a membrane-forming polymer can be a hydrophobic polymer. This different polymer used as a membrane-forming polymer, if used, can be, as an option, at least one of polysulfone (PSF), polyethersulfone (PES), polyarylsulfone (PAS), polyarylethersulfone (PAES), polyvinylidene fluoride (PVDF), polyacrylonitrile (PAN), or any copolymer thereof.

A membrane-forming polymer other than the polysulfone-urethane copolymer, such as when commercially obtained, may be pre-combined with smaller amounts of other co-additives, such as antioxidants (e.g., Vitamin E), UV stabilizers, antiozonates, antifoams, plasticizers, processing aids, stearates, dyes, and/or colorants, and so forth, which can be tolerated in the membrane compositions of the present invention.

The organic solvent used to dissolve the polysulfone-urethane copolymer and any different polymer used as membrane-forming polymer can be, as an option, at least one of dimethylacetamide (DMAC), dimethylformamide (DMF), tetrahydrofuran (THF), N-methylpyrrolidone (NMP), N-ethyl-2-pyrrolidone (NEP), dimethylsulfoxide (DMSO), tetrahydrofuran (THF), N-ethylpyrrolidone (NEP), N-octylpyrrolidone, dimethylformamide (DMF), or butyrolactone. As a preferred option, the organic solvent used to dissolve the polysulfone-urethane copolymer and any different polymer(s) used as membrane-forming polymer is a polar aprotic solvent. The organic solvent (e.g., polar aprotic solvent) can dissolve the polysulfone-urethane copolymer and any different polymer(s) used as membrane-forming polymer used for making the microporous membrane, e.g., by wet phase inversion process.

The polymer dope solution, as an option, can further comprise at least one hydrophilic polymer, such as polyvinylpyrrolidone (PVP) or polyethylene glycol (PEG), or other hydrophilic polymers. As indicated, the polysulfone-polyurethane copolymers according to the present invention can be used to reduce or even eliminate the amount of use of more highly leachable pore-forming additives, such as polyvinyl pyrrolidone (PVP) or polyethylene glycol (PEG), in membranes or other products. As an option, membranes formed using the polysulfone-urethane copolymer according to the invention can contain from 0 to less than 50 wt %, or from 0 to less than 25 wt %, or from 0 to less than 10 wt %, or from 0 to less than 5 wt %, or from 0 to less than 1 wt %, or from 1 to less than 50 wt %, or from 2 to less than 25 wt %, or from 3 to less than 10 wt %, or other amounts, of polyvinylpyrrolidone or polyethylene glycol, or both, based on total weight of the polymer dope solution. Thus, the polysulfone-polyurethane copolymers according to the present invention may effectively replace a conventional polysulfone/PVP membrane. If included, the amount of any hydrophilic polymer included in the polymer dope solution can be limited to amounts that do not cause a leaching problem.

The polymer dope solution can have limited or no water content. Premature coagulation of the polymer dope solution is undesirable to an extent that it would interfere with the ability of the polymer dope solution to extrude or cast or otherwise shape the polymer dope solution into a desired form of the membrane for contact with the precipitation fluid and/or to interact in the desired manner with the precipitation fluid. Water content of the polymer dope solution can be, as an option, less than about 7 wt % water, e.g., 0-6.9 wt % water, or 0-6 wt % or water, or 0-5 wt % water, or 0-4 wt % water, or 0-3 wt % water, or 0-2 wt % water, or 0-1 wt % water, or other amounts, based on total weight of the polymer dope solution.

The polymer dope solution can have a composition, as an option, of from about 1 wt % to about 30 wt % polysulfone-urethane copolymer, from about 0 to about 30 wt % membrane-forming polymer different from polysulfone-urethane copolymer, from about 88 wt % to about 63 wt % organic solvent (e.g., polar aprotic solvent), and less than about 7 wt % water, based on total weight of the polymer dope solution. In another option, the polymer dope solution can have a composition of from about 10 wt % to about 25 wt % polysulfone-urethane copolymer, from about from about 0 to about 30 wt % membrane-forming polymer different from polysulfone-urethane copolymer, from about 88 wt % to about 63 wt % polar aprotic solvent, and less than about 7 wt % water, based on total weight of the polymer dope solution. In another option, the polymer dope solution can have a composition of from about 13 wt % to about 20 wt % polysulfone-urethane copolymer, from about 87 wt % to about 75 wt % polar aprotic solvent, and less than about 6 wt % water, based on total weight of the polymer dope solution. Other compositions of the polymer dope solution which include these components may be used.

The precipitation fluid can comprise an organic solvent, such as a polar aprotic solvent, which can be selected from among the same solvents indicated for use with the polymer dope solution. The precipitation fluid also contains an inorganic solvent, such as water, in a sufficient amount in order to make possible precipitation of the polymer dope solution to the desired degree. In a preferred option, the inorganic solvent is water. As an option, sufficient water is included in the precipitation fluid such that the contacting of the precipitation fluid with the polymer dope solution can initiate coagulation in the formation of the membrane. As an option, the precipitation fluid contains at least about 25 wt % water, or at least about 30 wt % water, or from about 25 wt % to about 75 wt % water, or from about 30 wt % to about 70 wt % water, or other amounts, based on total weight of the precipitation fluid. The remainder of the precipitation fluid can be comprised of the organic solvent (e.g., polar aprotic solvent) and any additive(s). The precipitation fluid can have a composition, as an option, of from 75 wt % to about 25 wt % polar aprotic solvent and from about 75 wt % to about 25 wt % water, based on total weight of the precipitation fluid. In another option, the precipitation fluid comprises a composition of from about 70 wt % to about 30 wt % polar aprotic solvent and from about 70 wt % to about 30 wt % water, based on total weight of the precipitation fluid.

Where the microporous membrane is a hollow fiber, a hollow fiber can be produced in a method of the present invention, as an option, which comprises extruding or wet spinning the polymer dope solution through an outer ring duct of a spinneret comprising the outer ring duct and an internal hollow core, and simultaneously, passing the precipitation fluid through the internal hollow core, wherein the precipitation fluid acts directly on the polymer dope solution after issuing from the spinneret. The spun fiber can be cast into an aqueous washing bath with an air gap provided between the spinneret and aqueous washing bath. Precipitation of dope solution can initiate as the precipitation fluid comes in contact with the precipitation fluid. The precipitation process can continue into an aqueous washing bath. After precipitation, the coagulated fiber can be rinsed in a bath that can contain water and in which the hollow fiber can be temporarily held for washing out dissolved organic liquid constituents and for fixing the microporous structure of the fiber. After that, the fiber can be passed through a hot drying zone. The hollow fiber optionally can be texturized in order to improve the exchange properties thereof. After this, the fiber so produced can be handled in conventional manners, for example, by winding onto a bobbin, cutting the fibers to a desired length, bundled, and/or used in manufacture of dialyzers from the cut fiber in conventional manners.

A wet-spinning spinneret which can be used for spinning hollow fibers of the present invention can be types, for example, shown in U.S. Pat. Nos. 3,691,068; 4,906,375; and 4,051,300, all of which are incorporated in their entireties by reference herein. The indicated polymer dope solution containing the fiber forming polymer and organic solvent can be pumped to an annular extrusion spinneret having concentric tubes. The spinneret or nozzle, for example, can have a ring duct with a diameter equaling or approximating the desired outer diameter of the hollow fiber. For example, as wet spinning dimensions, the outer diameter orifice can be, as an option, from about 0.2 mm to 0.5 mm and the inner diameter can be from about 0.1 mm to about 0.4 mm, or other suitable sizes. A spinneret hollow core can typically extrude solution coaxially into and through this duct through which the precipitating fluid is fed simultaneously with polymer dope solution being fed between the outer surface of the hollow core and inner bore of the ring duct. The precipitating fluid can be pumped through this hollow core so that the precipitating solution emerges from the core tip and contacts with the hollow fiber configuration that is made up of the extruded polymer dope solution. As indicated, a hollow fiber or capillary membrane can be formed by the precipitating fluid acting in an outward direction on the polymer solution after issuing from the wet-spinning spinneret.

The amount or ratio of the precipitating fluid supplied to the polymer dope solution in the spinneret can be dependent, for example, on the dimensions of the wet-spinning spinneret, that is to say, the dimensions of the finished hollow fiber. In this respect, it can be desirable, as an option, that the dimensions of the fiber upon precipitation are not changed from those of the hollow fiber configuration before precipitation but after extrusion. As an option, the amount of first composition of the active surface can be controlled by controlling the ratio of the precipitating fluid to the polymer dope solution. The ratios of the volumes used of precipitating fluid to polymer dope solution can be in a range, as an option, of from about 1:0.5 to about 1:4, or other values, given an equal flow rate of the precipitating fluid and of the polymer dope solution, to the area ratios of the hollow fiber, i.e. the ring-area formed by the polymeric substance and the area of the fiber lumen. The precipitating fluid can be supplied to the extruded configuration directly upstream from the spinneret such that the inner or lumen diameter of the extruded and not yet precipitated configuration generally corresponds to the dimensions of the ring spinneret, from which the material is extruded. It can be useful if the outer diameter of the hollow fibers, as an option, is equal to from about 0.1 mm to about 0.5 mm, whereas the thickness of the membrane can be from about 10 µm to 100 µm or from about 15 µm to 50 µm.

As an option, in the present application, one or more properties of the polysulfone (PSF) urethane copolymer can be modified, for instance, to change the precipitation kinetics of the PSF-urethane copolymer's polymer solution to fabricate ultrafiltration membranes with desirable pore size and/or size distribution. Some properties of the PSF-urethane copolymer that can influence precipitation kinetics of its polymer solution include, but are not limited to, the PSF-urethane copolymer's molecular weight, the molecular weight of the oligo- or polyurethane block, the molecular weight of the PSF block, the ratio of oligo- or polyurethane to PSF block, distribution of the polyurethane and PSF blocks within the PSF-urethane copolymer, distribution of the hydrophilic and hydrophobic blocks within the PSF copolymer, and/or hydrophilicity of the copolymer. Any one or more of these properties can be altered or adjusted in the present invention as part of the method and resulting product. For example, the hydrophilicity of the PSF-urethane copolymer can be enhanced by employing an oligo- or polyurethane block based on polyethylene glycol, rather than polypropylene glycol. The hydrophilicity of the PSF copolymer can be enhanced by increasing the ratio of the oligo- or polyurethane to PSF block. In combination with the properties of the PSF-urethane copolymer, precipitation conditions of PSF copolymer's polymer solution can be controlled to change its precipitation kinetics to fabricate ultrafiltration membranes with desirable pore size and/or size distribution. These precipitation conditions include concentration of the PSF-urethane copolymer solution, precipitation temperature, and composition of the precipitating medium.

By controlling pore size and size distribution of the PSF-urethane copolymer-based ultrafiltration membranes, membranes with desired molecular weight cut off (MWCO) can be fabricated for applications in hemodialysis. In this way, a membrane having a MWCO of about 50 kDa, 55 kDa, 60 kDa, 65 kDa, 70 kDa, 75 kDa, 80 kDa, 85 kDa, 90 kDa, 95 kDa, 100 kDa, 110 kDa, 120 kDa, 130 kDa, 140 kDa, 150 kDa, or even higher than 150 kDa (e.g., from about 50 kDa to 150 kDa or more) can be obtained. Optionally, a lower MWCO may be desired, such as 30-40 kDa or 40-50 kDa. One option for achieving a desired MWCO value or range is to react the urethane block with a pre-formed polysulfone and "stalling" the reaction once the desired MWCO is reached.

As indicated, the present invention can be applied to fabrication of flat sheet membranes. The polymer dope solution containing the membrane-forming polymer and solvent can be coated and solidified in place as a continuous or discontinuous coating or film on a substrate surface (e.g., woven or non-woven). In a method of the present invention for making a flat sheet membrane, as an option, the polymer dope solution can be cast onto a surface of a carrier using a doctor blade or knife to provide a film-coated carrier, wherein the film is the polymer dope solution. Then, the film-coated carrier can be conveyed through a precipitation bath containing a precipitation fluid and further processed as needed to provide a microporous membrane containing product. Flat sheet casting procedures, such as described in U.S. Pat. No. 3,615,024, which is incorporated in its entirety by reference herein, may be adapted to make flat sheet membranes that incorporate polysulfone-urethane copolymer according to the present invention. In some aspects, a flat sheet membrane or hollow fiber membrane may be formed substantially from a polysulfone-urethane copolymer, without the need for an additional hydrophilic polymer.

The microporous membranes of the present invention can be used, as an option, for dialysis membranes, ultrafiltration membranes, and microfiltration membranes. The dialysis membranes can be, for example, hemodialysis membranes or hemofilters. Semi-permeable membrane filtration is often used in the purification of proteins, microfiltration and ultrafiltration being the most commonly practiced techniques. Microfiltration can be defined as a low pressure membrane filtration process which removes suspended solids and colloids generally larger than 0.1 µm in diameter. Such processes can be used to separate particles or microbes that can be seen with the aid of a microscope such as cells, macrophage, and cellular debris. Ultrafiltration membranes are characterized by pore sizes which enable them to retain macromolecules having a molecular weight ranging from about 500 Daltons to about 1,000,000 Daltons. Ultrafiltration is a low-pressure membrane filtration process which separates solutes in a range of from about 0.01 µm to 0.1 µm. Ultrafiltration can be used for concentrating proteins, and removing bacteria and viruses from a solution. Ultrafiltration also can be used for purification treatments, such as water purification. Dialysis membranes can be ultrafiltration membranes which comprise biocompatible materials, such as polyarylether polymer materials shown herein. When the membranes are hollow fibers, as an option, the hollow fibers can be microporous and capable of withstanding up to about 2,000 psi or more applied pressure without collapse, which refers to pressure applied from outside of the fiber. The hollow fibers, as an option, can have a fiber burst pressure of up to about 500 psi, which refers to pressure applied from the inner lumen side of the fiber.

The present invention further can relate to a process of using the microporous membrane for at least one of membrane filtering or solute and/or solvent exchange which can comprise contacting aqueous-based fluid or contacting blood with the microporous membrane described herein. A process for dialysis, blood oxygenation, or blood separation filtering of the present invention can comprise contacting blood with a microporous membrane as described herein.

As an option, the polysulfone-urethane copolymer may be incorporated into melted polymer material that is extrusion molded or molded in dies (e.g., injection molding) into products, such as medical products.

The present invention will be further clarified by the following examples, which are intended to be only exemplary of the present invention. Unless indicated otherwise, all amounts, percentages, ratios and the like used herein are by weight.

EXAMPLES

Example 1

Polysulfone-urethane copolymers of the present invention were synthesized.

(a) Materials

Materials and reagents used in the copolymer synthesis are listed in Table 1 with their common acronym.

TABLE 1

Materials and Reagents

| Name | Acronym |
|---|---|
| 4,4'-dichlorodiphenylsulphone | DCDPS |
| Bisphenol-A | BPA |
| Potassium carbonate | $K_2CO_3$ |
| Dimethylacetamide | DMAC |
| Urethane block (Poly(propylene glycol), Tolylene 2,4-Diisocyanate* | PPG-TDI |

*A narrowly distributed diisocyanate with molecular weight average Mn ~2,300, degree of polymerization ~34, composed of ~3.6 wt. % isocyanate (NCO).

(b) General Copolymer Synthesis Procedure Used:

The polysulfone urethane (PSF-Urethane) copolymer synthesis proceeded in a two-stage process. In the first stage, the urethane blocks were end-capped with BPA. Then, the polysulfone-urethane copolymer was synthesized in the second stage.

In order to incorporate the urethane oligomer into the polysulfone backbone in the second stage, the TDI end groups of the urethane block were first end-capped with BPA. This formed an oligomer with BPA on either end, which was reacted with DCDPS in the presence of $K_2CO_3$ to form the PSF-urethane block copolymer.

(i) BPA End Capping of PPG-TDI Urethane:

The BPA-oligomer end-capping (first stage) was achieved by reaction of the isocyanate (NCO) end groups of PPG-TDI in DMAC with excess BPA.

An oil jacketed 1-liter round bottom reactor vessel, fitted with a lid, was set up to accommodate an agitator shaft with two 4-blade impellers, a temperature probe, a nitrogen inlet, a charge port, and a neck attached to a Dean-Stark trap configured with a condenser above it. The reactor temperature was monitored so that the system pressure remained at atmospheric pressure, and the oil jacket, connected to an external circulator, maintained the desired temperature of the reactor contents.

First, a 15 wt-% BPA in DMAC solution was prepared by adding 135.00 g BPA to 765.00 g DMAC in a 1-liter media bottle and mixed until dissolved.

Then, 500 g of the 15 wt-% BPA solution was charged to the reactor, and the heating element was set to 67° C. in order to target a reactor solution temperature of 65° C. Agitation was set at a speed of 300 rpm, and nitrogen flow was set to 100 ml/min.

An additional 100 g of DMAC was charged to the reactor, and the contents were allowed to reach the target temperature under agitation.

Once the reactor contents reached a stable temperature at 65° C., the PPG-TDI solution was added. The charge port was fitted with a cap through which a ¼" stainless steel (SS) tube inlet was inserted, and the tubing was attached to a syringe pump. The urethane solution was weighed in a 60 mL syringe and then attached to the syringe pump to be gradually added to the reactor at a rate of 5 mL/min. During addition, the reactor was monitored to ensure the temperature remained at 65° C.±5° C. The syringe was refilled, weighed, and reattached to the syringe pump until 400 g of the PPG-TDI urethane had been added, or until the reaction vessel contained 40% urethane.

Once all the urethane was added, a 5-10 mL sample was taken immediately to have an initial NCO concentration measured in order to monitor the end-capping via NCO titration. The solution was allowed to react with BPA at a temperature of 65° C. for a minimum of 2 hours or until no change was seen in the amount or NCO end groups. The final sample analyzed was calculated to have ~0.21% NCO end groups ($t_0$≈0.41% NCO, blank≈0.2%). The solution was cooled to 40° C. and then stored in an amber colored bottle at ambient conditions.

(ii) Copolymerization: Two batches of polysulfone copolymer, each with different compositions of urethane, were synthesized using the BPA-end-capped PPG-TDI urethane. The copolymerization process of polysulfone and the urethane was used to form a block copolymer solution in DMAC, which would result in the polysulfone-urethane blocks.

A 2-Liter round bottom reactor vessel was charged with the appropriate amounts of DCDPS, $K_2CO_3$, DMAC, and 80% of a normal charge of BPA. The amount of BPA required for complete polymerization (i.e. 100%) of the DCDPS, charged to the reactor was considered as normal charge of BPA. The additional BPA required for the copolymerization was charged during the BPA end-capping of the urethane. The final molar ratio of the reaction solution was 0.9840 moles BPA to 1.0000 moles DCDPS. The BPA end-capped urethane was charged in the amounts of ~16 wt % or ~50 wt % to that of the targeted copolymer weight. The targeted copolymer weight is a theoretical number, calculated based on the amounts of free BPA, BPA end-capped urethane and DCDPS used. Using $K_2CO_3$ as a catalyst, the BPA end-capped urethane solution formed a bisphenol A salt anion, which competed with the free BPA for the DCDPS. This allowed the urethane blocks to be incorporated into the PSF polymer chain.

(c) Specific Copolymer Synthesis Procedures Used for Copolymer Batches 1 and 2:

PSF-Urethane Copolymer Synthesis Batch 1

PSF-urethane copolymer with theoretical ratio of 16 wt % BPA end-capped urethane to copolymer was synthesized.

The batch size and mass balance were established for production of 511.19 g of the PSF-PU copolymer. A 2-liter round-bottom reactor with a four neck reactor head was set up with an agitator with two A320 type impellers, a charging port and nitrogen inlet, fractionation column (Dean-Stark trap and water-cooled condenser), and a thermocouple. The Dean-Stark trap and reactor head were fitted with a heating tape and heating mantle, respectively. These were controlled by Variacs® and set at 25% for the tape and 50% for the mantle.

First, 200 g of the BPA end-capped urethane solution was charged into the reactor. Then, 334.36 g DCDPS and 170.58 g $K_2CO_3$ were added; $K_2CO_3$ was added in 6 wt % excess. An additional 246.55 g of BPA was added, and 465 g of DMAC was used to wash any residual reagents from the funnel and to achieve a reactor concentration of 47% soluble solids. Nitrogen flow was enabled after all additions and was monitored and adjusted throughout the reaction process in order to maintain a vapor temperature ~100° C. The nitrogen flow rate was typically between 254 and 459 ml/min. The reactor was lowered into a hot oil bath, which was set to heat the reactor to 150° C.-158° C. The overhead agitator was set to 300 rpm and increased to 500 rpm once solution viscosity began to increase.

Distillate was collected every hour from the Dean-Stark trap into a tared Erlenmeyer flask. The difference from the flask weight before and after was used to determine the amount of DMAC needed to be added back to the reactor in order to maintain the solution concentration throughout the reaction duration. The DMAC additions were made by using a syringe and dispensing the equivalent amount of DMAC to the amount of distillate removed. Karl Fisher titration of the distillate was used to determine the amount of expected water removed from the reaction.

A molecular weight (Mw) of 77,400-81,000 Daltons was targeted.

The reactor temperature reached 152° C. in ~2 hours and was maintained at 152-155° C. throughout the entire reaction. After 10 hours, 60% of the water was removed, and the agitator torque, which is used to monitor viscosity, increased. By 18 hours, 80% of the water had been removed, and the GPC results showed an Mw of 20,000 Daltons. Polymerization slowed after 38 hours with an Mw of 70,000 Daltons. Since the BPA to DCDPS stoichiometry was not 1:1, the reaction could be spiked with a slight amount of BPA if the Mw growth stalled at a lower Mw than desired. Therefore, a predetermined amount of BPA was added to reinitiate polymerization. After 45 hours, the Mw reached 77,000 Daltons. The reaction was stopped by adding 300 g of cold DMAC to lower the reactor temperature to 125° C. The contents were then poured into a larger flask and diluted with 1086 g DMAC to 20% soluble solids. The final molecular weight distribution was: Mn=22,000; Mw=77,300; and cyclic dimer content=1.15%.

The 20% solution was filtered through a 2 μm sintered metal disc using nitrogen pressure. After filtration was complete, the polymer was precipitated by slowly adding a 200 mL aliquot of the polymer solution into a blender with 2 L of deionized water (DI H$_2$O). It was then blended for an additional 1 to 2 minutes on high speed in order to remove most of the DMAC and to precipitate the polymer, which was then ground by the blender into a powder. When the blender was stopped, the contents were poured into a 25-50 μm vacuum filter funnel. The filtrate of DMAC and H$_2$O was discarded into a waste container. The polymer was returned to the blender with 1 L of fresh DI H$_2$O, and the process was repeated. After the second vacuum filtration, the polymer was placed in a tray and dried in an oven at 120° C. for >12 hours. The precipitation and drying process was repeated until all of the filtered polymer solution had been precipitated and dried. A slightly off-white powder was obtained after precipitation and drying.

PSF-Urethane Copolymer Synthesis Batch 2

PSF-urethane copolymer with theoretical ratio of 50 wt % BPA end-capped urethane to copolymer was synthesized.

The batch size and mass balance were established for production of 483.75 g of Polysulfone. A 2-liter round-bottom reactor was set up as described in Batch 1.

First, 650.00 g of the BPA-end-capped urethane solution was charged to the reactor. Then, 316.49 g DCDPS and 167.56 g K$_2$CO$_3$ were added; K$_2$CO$_3$ was added in 10% excess. An additional 198.82 g of BPA was added, and an additional 205 g of DMAC was used to wash any residual reagents from the funnel and to achieve a reactor concentration of 47% soluble solids. Nitrogen flow was enabled and was monitored and adjusted throughout the reaction process in order to maintain a vapor temperature ~100° C. The nitrogen flow rate was typically between 254 and 459 ml/min. The reactor was lowered into a hot oil bath, which was set to heat the reactor to 150° C.-158° C. The overhead agitator was set to 300 rpm and increased to 500 once solution viscosity began to increase.

Distillate was collected every hour from the Dean-Stark trap, titrated, and DMAC was added back to the reactor, similarly to Batch 1. The target Mw was 77,400-81,000 Daltons. The reaction was monitored using GPC and torque as indicators for polymerization progress.

The reactor temperature reached 152° C. in ~2 hours and was maintained at 152-155° C. throughout the entire reaction. After 12 hours and 28 hours, 35% and 47% of the water was removed, respectively. The agitator torque began to increase at 20 hours, at which time the Mw was 10,600 Daltons. Water removal reached ~52% by 37 hours but the Mw was at 80,000, and polymerization seemed to be stalling. The reaction was allowed to continue until 44 hours had elapsed, and the final molecular weight distribution was measured by gas chromatography: Mn=19,500; Mw=88,000 Daltons; and cyclic dimer content=1.15%. The reaction was stopped by adding 300 g of cold DMAC to lower the reactor temperature to 125° C. This copolymer reactor solution was poured into the larger flask, the solution was observed to have a more slippery and rubberlike consistency than a standard polysulfone solution. An additional 1,086 g DMAC was added to dilute the solution to 20% soluble solids. The 20% polymer solution was precipitated, filtered, and dried as described in Batch 1.

(d) Results of the Copolymer Synthesis

A summary of the two batches of the polysulfone-urethane copolymers synthesized in Batches 1 and 2 is presented in Table 2. Molecular weight distribution of the polysulfone-urethane copolymers, from GPC analysis, was compared with that of a typical polysulfone (i.e., UDEL® P-3500 polysulfone from Solvay). It was observed that the molecular weight distribution of the inventive polysulfone-urethane copolymers was noticeably different from that of the typical polysulfone. For both batches of polysulfone-urethane copolymers synthesized, it was apparent that there was some higher molecular weight material before the main polymer peak eludes. For the copolymer with BPA end-capped urethane composition of 50 wt-%, molecular weight distribution of the final copolymer solution and the precipitated copolymer were plotted and compared with UDEL® P-3500 polysulfone from Solvay in overlaid GPA chromatograms (not shown). This overlay showed that both the polymer solution and precipitated polymer powder have the same molecular weight distribution.

TABLE 2

Summary of the PSF Copolymer Synthesis

| Synthesis Batch | BPA endcapped-Urethane composition in PSF copolymer (Wt %)* | Mn | Mw |
|---|---|---|---|
| 1 | ~16 | 22,000 | 77,300 |
| 2 | ~50 | 19,500 | 88,000 |

*Theoretical number based on the amounts of reactants used for copolymer synthesis.

Example 2

Flat sheet membranes were cast with polymer dope solutions containing the polysulfone-urethane copolymers of Batches 1 and 2 of Example 1 and characterized.

(a) Preparation of the Polymer Dope Solutions:

Polymer dope solutions specific for casting flat sheet membranes were prepared by adding known amounts of the base polymer, additive (e.g. polyvinylpyrrolidone, PVP), and solvent (e.g. dimethylacetamide, DMAC). Components were mixed at 70° C. until the polymer and additives were completely dissolved in the solvent. Different dope solutions were mixed containing polysulfone (UDEL® P-3500 from Solvay) or the synthesized polysulfone-urethane copolymer (Batch 1 or Batch 2) as the base polymer; PV) (K-90 from Ashland) was used as an additive; DMAC was used as the solvent. Amount of solids (i.e. base polymer and additives) in all of the polymer dope solutions was about 19 to 20 wt-%.

(b) Procedure for Casting Flat Sheet Membranes:

Flat sheet membranes were cast, precipitated, and rinsed at ambient conditions. Casting began with about 15 mL of the dope solution dispensed at one end of a level glass plate. Using a doctor blade that was adjusted to a known blade height, the dope solution was spread uniformly on the glass plate to make a thin film measuring 9 inches×12 inches. Immediately after spreading the solution, the glass plate was completely submerged in a known concentration of a precipitation solution (percent DI H$_2$O in DMAC) for five minutes to precipitate the polymer dope solution into a flat sheet membrane.

The flat sheet was rinsed on the glass plate, for ease of handling, in a DI H$_2$O bath for 10 minutes. Lastly, the flat sheet was dried as a loose film at room temperature for at least 24 hours before any testing was performed.

(c) Procedure for Testing the Flat Sheet Membranes

After the flat sheets were completely dried, the membranes were cut into 43 mm diameter disks to be tested for water permeance and dextran sieving coefficient.

The membrane disks were placed into a flat sheet membrane test cell (Advantec, UHP 43) with the active side of the membrane facing upwards. The active side was defined as the side exposed to air during casting on the glass plate. The membrane cell was filled with feed solution, water or dextran solution, and pressurized to the desired pressure (10-15 psi) using a nitrogen gas cylinder.

The Dextran sieving procedure and dextran sieving coefficient was determined using internal GPC procedures. Briefly, feed solutions including dextrans of different molecular weights was filtered across the membrane. Feed, retentate and permeate samples were then analyzed for concentration of dextran's using Gel Permeation Chromatography (GPC). The Dextran sieving coefficient was calculated based on these measured concentrations.

(d) Results (i) Water Permeance:

PSF Copolymer Batch 1 (16 wt % BPA end capped-urethane block composition):

Flat sheet membranes were cast from polymer dope solutions having different ratios of PSF-urethane copolymer to PVP in order to study the amount of PVP additive required to make a porous and hydrophilic membrane. For comparison, membranes were also cast using polymer solution of UDEL® P-3500 PSF containing different amounts of PVP additive. Both the PSF-Urethane copolymer and UDEL® P-3500 PSF-based membranes were made using a 20 wt-% precipitation fluid. Water permeance was used as a measure to study the porosity and hydrophilicity of the flat sheet membranes.

Figure 7:
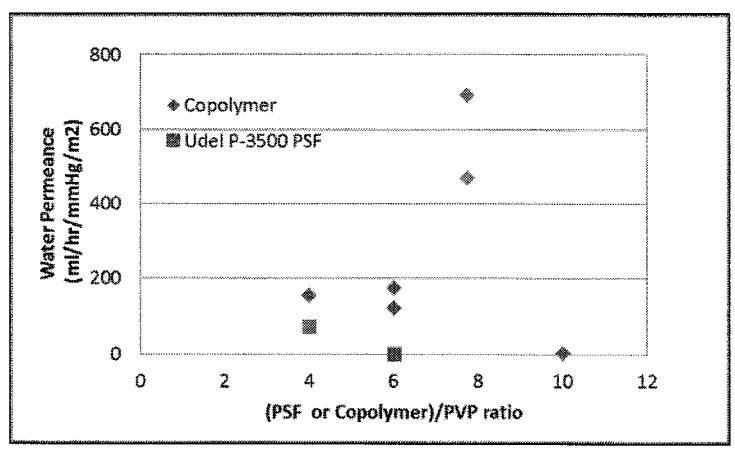
FIG. 7 shows a plot of water permeance for flat sheet membranes formed with different ratios of inventive polysulfone-urethane copolymer (Batch 1: 16 wt % BPA end-capped urethane/copolymer) to PVP, according to an example of the present application, and membranes formed with different ratios of comparative polysulfone to PVP.

The PSF-urethane copolymer based membranes representing examples of the present invention had a higher water flux compared to UDEL® P-3500 PSF-based membranes (Solvay Specialty Polymers); see FIG. 7 (♦ represents PSF-urethane copolymer data, ■ represents UDEL® P-3500 PSF data). At a base-polymer/PVP ratio of 6.0, water permeance of the PSF-Urethane copolymer membrane was 123 ml/hr/mmHg/m$^2$, while the UDEL® P-3500 PSF-based membrane was 0 ml/hr/mmHg/m$^2$. Similarly, when the copolymer was cast with no PVP additive, the water permeance was 0 ml/hr/mmHg/m$^2$. The PSF-Urethane copolymer based membranes have a urethane block that is hydrophilic, which could be contributing to the pore formation and/or hydrophilicity of the membranes resulting in the higher water permeance, relative to the UDEL® P-3500 PSF-based membranes. However, the copolymer cast membrane with 16 wt % may benefit from the use of pore forming additive(s) such as PVP to better ensure a sufficient volume fraction of urethane blocks for porous and hydrophilic membranes.

PSF Copolymer Batch 2 (50 wt % BPA end capped-urethane block composition):

Flat sheet membranes were made using the PSF-urethane copolymer without any PVP additive. The effect of precipitation fluid composition on water permeance was studied for the PSF copolymer membranes; see FIG. 8 (♦ represents PSF-urethane copolymer data, ■ represents UDEL® P-3500 PSF data). Water permeance was measured for all membranes casted using the copolymer, even without any PVP. The 50 wt-% BPA end-capped urethane copolymer contained enough urethane blocks to form a porous and hydrophilic membrane without any pore forming additive such as PVP.

Figure 8:
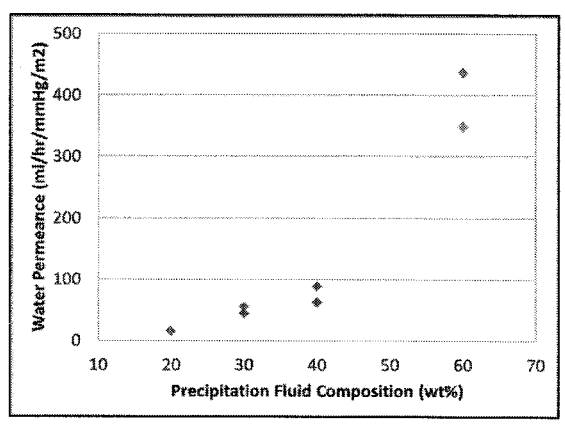
FIG. 8 shows a plot of water permeance for flat sheet membranes formed with different ratios of inventive polysulfone-urethane copolymer (Batch 2: 50 wt % BPA end-capped urethane/copolymer) to PVP, according to an example of the present application, and membranes formed with different ratios of comparative polysulfone to PVP.

Water permeance of the PSF-urethane copolymer membranes increased with an increase in water content of the precipitation fluid; see FIG. 8. Conversely when water soluble pore forming additive such as PVP was blended with UDEL® P-3500 PSF and cast into flat sheet membranes, water permeance decreased with an increase in water content of the precipitation fluid.

The urethane blocks of the PSF-urethane copolymer were hydrophilic, and therefore water in the precipitation fluid may not be acting as effectively as a non-solvent during the precipitation of the polymer solution. Presence of the urethane block may have a significant influence on precipitation kinetics of the polymer. Therefore, the properties of the urethane block and its composition in the PSF-urethane copolymer can be used as a tool to control the precipitation kinetics of the polymer solution and hence the membrane properties.

(ii) Dextran Sieving:

Membranes made from the PSF copolymer with BPA end-capped urethane block composition of about 50 wt-% (without any PVP additive) were studied for dextran sieving coefficient. Sieving coefficient of the membrane with the lowest water permeance (i.e. 15 ml/hr/mmHg/m$^2$) in the dextran's molecular weight range of 10K to 100K Daltons was about one; i.e., all dextran molecules within the studied molecular weight range were permeating across the membrane without any rejection. The pore dimensions of the membrane were likely to be in the range of microfiltration membranes. However, for the purpose of dialysis treatment and blood purification, the pore dimensions are required to be in the range of ultrafiltration; either the PSF copolymer properties or precipitation kinetics of the dope solution will have to be modified.

Figure 9A:
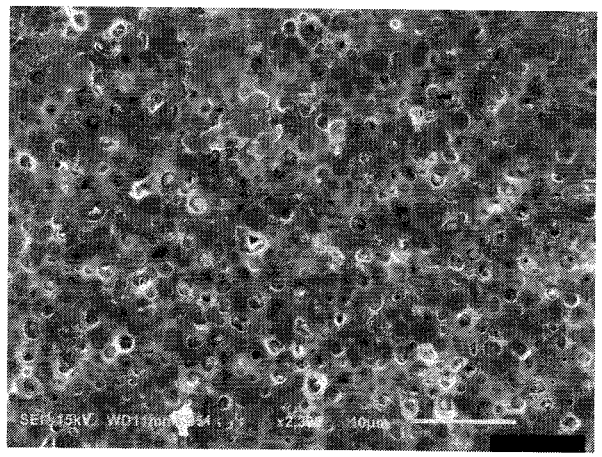
FIG. 9A is an SEM image of a bottom surface of porous copolymer membrane formed with polysulfone-urethane copolymer of Batch 2 without PVP.
Figure 9B:
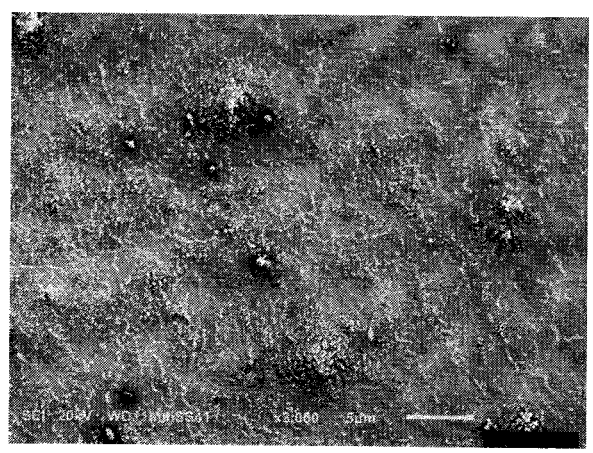
FIG. 9B is an SEM image of the top surface (active side) of the membrane, according to an example of the present application.

(iii) SEM Analysis:

Visual surface analysis via SEM indicated a porous surface on the top and bottom of the flat sheet membrane that was cast with the PSF-urethane copolymer without PVP additive; see FIGS. 9A-9B. Since precipitation of the polymer solution during casting of the flat sheet membrane was initiated from the top surface, it was expected that the top surface of the membrane would have a denser pore structure compared to the bottom surface.

Summary

Two batches of PSF-urethane copolymer were successfully synthesized in a two stage synthesis process. The PPG-TDI urethane was first end-capped with BPA, and then introduced to DCDPS at various weights to produce a 16 wt % and 50 wt % BPA end-capped urethane composition to the final copolymer target weight. The molecular weights were 77,300 Da (16 wt-% BPA end-capped urethane composition) and 88,000 Da (50 wt-% 16 wt % BPA end-capped urethane composition); see Table 2.

The 50 wt-% BPA end-capped urethane composition copolymer was cast into a porous and hydrophilic flat sheet membrane without any pore forming additive, i.e. PVP. The 16 wt-% BPA end-capped urethane composition copolymer required PVP, but less than the UDEL® P-3500 PSF to make a porous membrane; see FIG. 7. Visual observations via SEM confirmed porous structure on the top and bottom of the membrane; see FIGS. 9A-9B.

Water permeance of the 50 wt-% BPA end-capped urethane composition copolymer flat sheet membrane without any PVP additive increased with an increase in water composition of the precipitation fluid; see FIG. 8.

Dextran sieving of the 50 wt % BPA end-capped urethane composition copolymer flat sheet membrane could have a molecular weight cutoff >100 kDa.

Since the application for the PSF-urethane copolymer was targeted for dialysis and blood purification, the pore size must be reduced significantly. Future studies are to include modifying the pore structure for a lower molecular weight cut off by altering the PSF copolymer urethane composition or the precipitation kinetics via casting.

The present invention includes the following aspects/embodiments/features in any order and/or in any combination:

1. The present invention relates to a polysulfone-urethane copolymer comprising formula (I) or formula (II):

$$[D-E]_{a1}\text{-}[D\text{-}G\text{-}D]_{a2}\text{-}[E\text{-}D]_{a3} \quad (I)$$

$$[D\text{-}(E\text{-}D)_{b1}\text{-}(G)_{b2}\text{-}(D\text{-}E)_{b3}]_{b4} \quad (II)$$

wherein G is a urethane block, D is a divalent residue of an aromatic dihydroxyl compound, E is an aromatic sulfone group, and wherein i) a1, a2 and a3 are independently from 1-100 which randomly or non-randomly repeat in formula (I), and ii) b1, b2, b3, and b4 are independently from 1-100 which randomly or non-randomly repeat in formula (II).

2. The polysulfone-urethane copolymer of any preceding or following embodiment/feature/aspect, having formula (I):

$$[D-E]_{a1}\text{-}[D\text{-}G\text{-}D]_{a2}\text{-}[E\text{-}D]_{a3}$$

wherein a1 and a3 are independently from 10-100 and a2 is from 1-10 units which randomly or non-randomly repeat in formula (I).

3. The polysulfone-urethane copolymer of any preceding or following embodiment/feature/aspect, having formula (II):

$$[D\text{-}(E\text{-}D)_{b1}\text{-}(G)_{b2}\text{-}(D\text{-}E)_{b3}]_{b4}$$

wherein b1 and b3 are independently from 10-100 and b2 and b4 are independently from 1-10 units which randomly or non-randomly repeat in formula (II).

4. The polysulfone-urethane copolymer of any preceding or following embodiment/feature/aspect, having formula (III):

$$J\text{-}D\text{-}[X]_g\text{-}[D\text{-}G\text{-}D]_y\text{-}[X]_i\text{-}D\text{-}J$$

wherein J is an end group of the polymer, X is a polysulfone block comprised of aromatic dihydroxyl compound and dihalodiphenyl sulfone, wherein g and i are independently from 1-100 units.

5. The polysulfone-urethane copolymer of any preceding or following embodiment/feature/aspect, wherein each J is a mono-reacted residue of a dihalodiphenyl sulfone or a polysulfone block containing an aromatic dihydroxyl compound and a dihalodiphenyl sulfone end unit.

6. The polysulfone-urethane copolymer of any preceding or following embodiment/feature/aspect, wherein each E is a di-reacted residue of a dihalodiphenyl sulfone.

7. The polysulfone-urethane copolymer of any preceding or following embodiment/feature/aspect, wherein D is a di-reacted residue of a dihydroxydiphenyl sulfone or a dihydroxybiphenyl.

8. The polysulfone-urethane copolymer of any preceding or following embodiment/feature/aspect, wherein G comprises an oligo- or polyurethane chain of formula (IV):

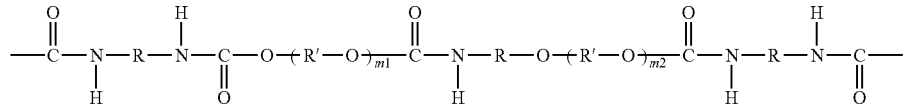
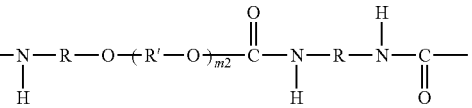

wherein R is a divalent residue of an aliphatic or aromatic diisocyanate linker, R' is a divalent residue of an organic polyol compound which is different from D, m1 is 1-10, and m2 is 0-10.

9. The polysulfone-urethane copolymer of any preceding or following embodiment/feature/aspect, wherein the G further comprises at least one amphiphilic or hydrophobic block in the oligo- or polyurethane chain.

10. The polysulfone-urethane copolymer of any preceding or following embodiment/feature/aspect, wherein D is of formula (V):

—O—Ar-L—Ar'—O— wherein each of Ar and Ar' is an aromatic moiety; L is a linking moiety selected from $L^1$ or $L^2$, wherein $L^1$ has the formula (VI):

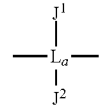

wherein $L_a$ alkyl or alkylaralkyl, wherein each of $J^1$ and $J^2$ is independently selected from hydrogen, alkyl, halogenated alkyl, halogenated arylalkyl, alkenyl, haloalkenyl, phenyl, halogen, hydroxyalkyl, hydroxyarylalkyl, alkynyl, alkyloxy, arylalkyloxy, aminoalkyl, aminoarylalkyl, alkyl and arylalkyl substituted by carboxylic acid, ester, amide, aldehyde and ketone function, and $L^2$ is $SO_2$.

11. The polysulfone-urethane copolymer of any preceding or following embodiment/feature/aspect, wherein E is of formula (VII):

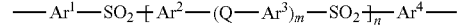

wherein each of m and n are independently zero or an integer of 1 to 10; each of $Ar^1$, $Ar^2$, $Ar^3$ and $Ar^4$ is an unsubstituted or substituted aromatic moiety; Q is a bond or a divalent group.

12. The polysulfone-urethane copolymer of any preceding or following embodiment/feature/aspect, wherein one or more of $Ar^1$, $Ar^2$, $Ar^3$ and $Ar^4$ is a substituted aromatic moiety comprising at least one substituent selected from haloalkyl and quaternary amine.

13. The polysulfone-urethane copolymer of any preceding or following embodiment/feature/aspect, wherein Q is a bond, unsubstituted or substituted phenyl, —$CH_2$—, —C(O), —$C(CH_3)_2$—, —$C(CF_3)_2$—, —C(—$CCl_2$), or —$C(CH_3)(CH_2CH_2COOH)$—.

14. The polysulfone-urethane copolymer of any preceding or following embodiment/feature/aspect, which has a weight average molecular weight of from about 10,000 to about 750,000 g/mol.

15. The present invention relates to a polymer composition comprising the polysulfone-urethane copolymer of any preceding or following embodiment/feature/aspect in an amount of from about 10% to about 100% by weight of total weight of the polymer composition.
16. The present invention relates to a membrane comprising the polysulfone-urethane copolymer of any preceding or following embodiment/feature/aspect.
17. The membrane of any preceding or following embodiment/feature/aspect, wherein the membrane is a hollow fiber or a flat sheet.
18. The membrane of any preceding or following embodiment/feature/aspect containing 0 to less than 50 wt % total polyvinylpyrrolidone or polyethylene glycol.
19. The present invention relates to a method for preparing a polysulfone-urethane copolymer, comprising:
    1) reacting at least one oligo- or polyurethane block with an aromatic dihydroxyl compound which end caps the at least one oligo- or polyurethane block to form an end-capped oligo- or polyurethane block; and
    2) reacting the end-capped oligo- or polyurethane block with an aromatic diol and a dihalodiphenyl sulfone to form a polysulfone-urethane copolymer with control of stoichiometry so that the polysulfone-urethane copolymer has dihalodiphenyl sulfone end groups.
20. The present invention relates to a method for preparing a polysulfone-urethane copolymer, comprising:
    1) reacting an aromatic diol and a dihalodiphenyl sulfone to form polysulfone block, and control the stoichiometry so that the polysulfone block is end-capped with residue of an aromatic diol; and
    2) reacting at least one oligo- or polyurethane block, an aromatic dihydroxyl compound, and the polysulfone block to form a polysulfone-urethane copolymer.
21. The present invention relates to a method for preparing a polysulfone-urethane copolymer, comprising:
    1) reacting aromatic diol and an excess dihalodiphenyl sulfone to form polysulfone block, and control the stoichiometry so that the polysulfone block has dihalodiphenyl end groups;
    2) reacting at least one oligo- or polyurethane block with an aromatic dihydroxyl compound which end caps the at least one oligo- or polyurethane block; and
    3) reacting the polysulfone block and the end-capped oligo- or polyurethane block to form a polysulfone-urethane copolymer.
22. The method of any preceding or following embodiment/feature/aspect, further comprising 4) adding a dihalodiphenyl sulfone and/or an aromatic diol to complete the polymerization or build molecular weight of the copolymer.
23. The method of any preceding or following embodiment/feature/aspect, further comprising preparing the at least one oligo- or polyurethane block by reacting diisocyanate and an organic polyol compound to form the at least one oligo- or polyurethane block.
24. The method of any of preceding or following embodiment/feature/aspect, further comprising separating low molecular weight species from the polysulfone-urethane copolymer.
25. The method of preceding or following embodiment/feature/aspect, wherein the low molecular weight species is one or more oligomers.
26. The method of any preceding or following embodiment/feature/aspect, wherein the reacting the at least one oligo- or polyurethane block with the aromatic dihydroxyl compound is performed in the presence of metal carbonate, aprotic polar solvent, and excess of the aromatic dihydroxyl compound.
27. The method of any preceding or following embodiment/feature/aspect, wherein the reacting of the end-capped oligo- or polyurethane block with the aromatic hydroxyl compound and the dihalodiphenyl sulfone is performed in the presence of metal carbonate and aprotic polar solvent.
28. The method of any preceding or following embodiment/feature/aspect, wherein the aromatic dihydroxyl compound is a bisphenol and the dihalodiphenyl sulfone is a 4,4'-dihalodiphenyl sulfone.
29. The method of any preceding or following embodiment/feature/aspect, further comprising at least one of modifying at least one terminal groups of the oligo- or polyurethane chain or incorporating at least one amphiphilic or hydrophobic block in the oligo- or polyurethane chain.
30. The method of any preceding or following embodiment/feature/aspect, further comprising adding at least functional group to at least one aryl group of at least one polysulfone block of the polysulfone-urethane copolymer, wherein the at least one functional group is selected from haloalkyl and quaternary amine.
31. A process of making a membrane comprising preparing a dope solution containing the polysulfone-urethane copolymer of any preceding or following embodiment/feature/aspect, and forming a hollow fiber or flat sheet with the dope solution.
32. The process of any preceding or following embodiment/feature/aspect, wherein the dope solution further comprises at least one of polysulfone, polyethersulfone, polyarylsulfone, polyarylethersulfone, polyvinylidene fluoride, polyacrylonitrile, or any copolymer thereof.
33. The present invention relates to a process of making a membrane, comprising:
    a) forming a spinning mass comprising the polysulfone-urethane copolymer of any preceding or following embodiment/feature/aspect; and
    b) spinning the spinning mass through a spinneret to form hollow fibers.
34. The process of any preceding or following embodiment/feature/aspect, wherein the spinning mass contains from 0 to less than 50 wt % total polyvinylpyrrolidone or polyethylene glycol.
35. The present invention relates to a dialyzer comprising hollow fibers of any preceding or following embodiment/feature/aspect.
36. The present invention relates to a process for hemodialysis or hemofiltration or hemodiafiltration comprising contacting blood with a membrane comprising at least one of the hollow fibers or flat sheet of any preceding or following embodiment/feature/aspect.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for preparing a polysulfone-urethane copolymer, comprising
   1) reacting an aromatic diol and a dihalodiphenyl sulfone to form a polysulfone block, and control the stoichiometry so that the polysulfone block has dihalodiphenyl end groups,
   2) reacting at least one oligo- or polyurethane block with an aromatic dihydroxyl compound which end caps the at least one oligo- or polyurethane block to form an encapped oligo- or polyurethane block, and
   3) reacting the polysulfone block and the end-capped oligo- or polyurethane block to form the polysulfone-urethane copolymer.

2. The method of claim 1, wherein said step 1) and said step 2) are conducted in the presence of at least one metal carbonate and at least one solvent.

3. The method of claim 2, wherein said metal carbonate is dipotassium carbonate and said solvent is a polar aprotic solvent.

4. The method of claim 1, wherein said polysulfone block having said dihalodiphenyl end groups comprises repeating units of an aromatic dihydroxyl compound and a dihalodiphenyl sulfone and a dihalodiphenyl sulfone end groups.

5. The method of claim 1, wherein said reacting in said step 1) is in the presence of a metal carbonate as a catalyst at a reaction temperature of from about 145° C. to about 185° C. for about 2 hours to about 12 hours in a reaction vessel setup with a fractionation column.

6. The method of claim 1, wherein said step 2) is maintained at a reaction temperature of 65° C.±5° C. at atmospheric pressure for at least 2 hours or until no change is seen in the amount of NCO end groups.

7. The method of claim 1, wherein in said step 3), said reacting is in the presence of a metal carbonate as catalyst at a reaction temperature of from about 145° C. to about 185° C. for about 2 hours to about 12 hours in a reaction vessel with a fractionation column.

8. The method of claim 2, wherein said solvent is dimethylacetamide (DMAC), dimethylformamide (DMF), tetrahydrofuran (THF), N-methylpyrrolidone (NMP), N-ethyl-2-pyrrolidone (NEP), dimethylsulfoxide (DMSO), tetrahydrofuran (THF), N-ethylpyrrolidone (NEP), N-octylpyrrolidone, dimethylformamide (DMF), butyrolactone, or sulfolane, anisole.

9. The method of claim 2, wherein said metal carbonate is anhydrous.

10. The method of claim 2, wherein said metal carbonate is an alkali metal carbonate, alkaline earth metal carbonate, or any combination thereof.

11. The method of claim 2, wherein said metal carbonate is sodium carbonate, potassium carbonate, and/or calcium carbonate.

12. The method of claim 2, wherein said metal carbonate is in dry fine particle form.

13. The method of claim 1, further comprising separating low molecular weight species from the polysulfone-urethane copolymer after said step 3), wherein the low molecular weight species is one or more oligomers.

14. The method of claim 1, wherein the reacting of the at least one oligo- or polyurethane block with the aromatic dihydroxyl compound is performed in the presence of a metal carbonate, an aprotic polar solvent, and an excess of the aromatic dihydroxyl compound.

15. The method of claim 1, wherein the aromatic dihydroxyl compound is a bisphenol and the dihalodiphenyl sulfone is a 4,4'-dihalodiphenyl sulfone, and said aromatic diol is the aromatic dihydroxyl compound.

16. The method of claim 1, said method further comprising at least one of modifying at least one terminal group of the oligo- or polyurethane block or incorporating at least one amphiphilic or hydrophobic block in the oligo- or polyurethane block.

17. The method of claim 1, said method further comprising adding at least one functional group to at least one aryl group of the polysulfone block of the polysulfone-urethane copolymer.

18. The method of claim 1, wherein said polysulfone-urethane copolymer comprises formula (III):

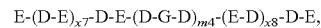

E-(D-E)$_{x7}$-D-E-(D-G-D)$_{m4}$-(E-D)$_{x8}$-D-E, wherein x7=1-100, m4=1-100, and x8=1-100 which randomly or non-randomly repeat in formula (III), and G is a urethane block, D is a divalent residue of an aromatic dihydroxyl compound, E is an aromatic sulfone group, and wherein the urethane block is a urethane from a reaction of a diisocyanate and a polyol and wherein the polyol is of the formula: HO—CH(Z)—CH$_2$—O)$_{n1}$—H, where Z is CH$_3$ or H and n1 is from 1 to 100.

19. The method of claim 18, wherein said x7=10-30, m4=1-10, and said x8=10-30.

20. The method of claim 18, wherein G is a series of urethane blocks.

21. The method of claim 1, said method further comprising adding at least functional group to at least one aryl group of the polysulfone block of the polysulfone-urethane copolymer, wherein the at least one functional group is selected from haloalkyl and quaternary amine.

* * * * *